United States Patent
Bobkova et al.

(10) Patent No.: US 10,143,722 B2
(45) Date of Patent: Dec. 4, 2018

(54) APPLICATION OF YB-1 PROTEIN AND FRAGMENTS THEREOF FOR PREPARING MEDICINAL AGENTS IN TREATING ALZHEIMER'S DISEASE

(71) Applicant: Maria Dupont, Huerth (DE)

(72) Inventors: Nataliya Viktorovna Bobkova, Puschino (RU); Lev Pavlovich Ovchinnikov, Puschino (RU); Nataliya Igorevna Medvinskaya, Puschino (RU); Sergey Georgevich Guryanov, Puschino (RU); Inna Vladimirovna Nesterova, Puschino (RU); Irina Alexandrovna Eliseeva, Puschino (RU); Alexandr Nikolaevich Samokhin, Puschino (RU); Irina Yurievna Alexandrova, Puschino (RU); Pavel Valerievich Nekrasov, Puschino (RU)

( * ) Notice: Subject to any disclaimer, the term of this patent is extended or adjusted under 35 U.S.C. 154(b) by 19 days.

(21) Appl. No.: 14/914,701

(22) PCT Filed: Aug. 21, 2014

(86) PCT No.: PCT/RU2014/000625
§ 371 (c)(1),
(2) Date: Feb. 26, 2016

(87) PCT Pub. No.: WO2015/030628
PCT Pub. Date: Mar. 5, 2015

(65) Prior Publication Data
US 2016/0331806 A1    Nov. 17, 2016

(30) Foreign Application Priority Data
Aug. 28, 2013 (RU) .................. 2013139704

(51) Int. Cl.
| | | |
|---|---|---|
| A61K 38/00 | (2006.01) | |
| A61K 38/17 | (2006.01) | |
| A61K 9/00 | (2006.01) | |
| A61K 45/06 | (2006.01) | |

(52) U.S. Cl.
CPC ........ *A61K 38/1709* (2013.01); *A61K 9/0043* (2013.01); *A61K 45/06* (2013.01)

(58) Field of Classification Search
None
See application file for complete search history.

(56) References Cited

U.S. PATENT DOCUMENTS

2007/0072795 A1    3/2007  Haselbeck et al.

FOREIGN PATENT DOCUMENTS

| EA | 1204 B1 | 9/1996 | |
|---|---|---|---|
| WO | WO-0244363 A1 * | 6/2002 | ......... C07K 14/4702 |
| WO | WO/2013/006076 A1 | 1/2013 | |

OTHER PUBLICATIONS

Ding et al Neuroscience let 399: 11-16, 2006.*
Wells, 1990, Biochemistry 29:8509-8517.*
Ngo et al., The Protein Folding Problem and Tertiary Structure Prediction, pp. 492-495, 1994.*
Bork, Genome Research 10:398-400, 2000.*
Skolnick et al., Trends in Biotech. 18(1):34-39, 2000.*
Doerks et al.,Trends in Genetics 14:248-250, 1998.*
Smith et al., Nature Biotechnology 15:1222-1223, 1997.*
Brenner, Trends in Genetics 15:132-133, 1999.*
Bork et al., Trends in Genetics 12:425-427, 1996.*
Halliday et al Clin Exp Pharmacol Physiol 27: 1-8, 2000.*
Steece-Collier et al., PNAS USA 99(22): 13972-13974, 2002.*
Feigin et al., Curr Opin Neurol 15: 483-489, 2002.*
Bobkova N.V. et al., The state of cholinergic forebrain structures in bulbectomized mice, Bull Exp Biol Med. 131:427-31(2001), RU.
Bobkova N.V. et al., Possible role of olfactory system in Alzheimer's disease genesis, in book «Alzheimer's and Parkinson's disease—AD/PD». Edit. L.Hanin, A.Fisher, Monduzzi. Medimond. 91-95 (2005).
Bobkova N.V., A model of sporadic Alzheimer's disease using bulbectomized animals, in book "Neurodegenerative diseases. Fundamental and applied aspects". Edit. M.V.Ugryumov. M. Nauka. 341-350 (2010) RU.
Niesterova I.V. et al., Morphofunctional state of neurons in the temporal cortex and hippocampus in relation to the level of spatial memory in rats after ablation of the olfactory bulbs, Neurosci. Behav. Physiol. 38(4):349-353 (2008).
Bobkova N.V. et al., Post-bulbectomy activation of compensatory mechanisms in the brain, Ross Fiziol Zh Im I M Sechenova, 90 (8): 199-200 (2004), RU.
Gavrilova S.I. et al., Alzheimer's disease: clinics and diagnostics, in book "Neurodegenerative diseases. Fundamental and applied aspects". Edit. M.V.Ugryumov. M. Nauka. 243-251 (2010), RU.
Bachurin S.O. et al., Modern approaches to treatment of Alzheimer's disease, in book "Neurodegenerative diseases. Fundamental and applied aspects". Edit. M.V.Ugryumov. M. Nauka. 313-340 (2010), RU.
Gavrilova S.I. et al., Social and environmental factors and the mental health of elderly people, Vestn Ross Akad Med Nauk. 9:15-20 (2002), RU.
Bertoni-Freddari C. et al., Deterioration threshold of synaptic morphology in aging and senile dementia of Alzheimer's type, Anal Quant Cytol Histol. 18(3):209-13 (1996), RU.

(Continued)

*Primary Examiner* — Daniel E Kolker
*Assistant Examiner* — Aditi Dutt
(74) *Attorney, Agent, or Firm* — Michael J. Feigin, Esq.; Feigin and Fridman LLC

(57) ABSTRACT

The present invention relates to the field of genetic engineering and medicine. Proposed is a method for treating neurodegenerative diseases and Alzheimer's disease that includes the intranasal administration to a subject of a therapeutically effective amount of the YB-1 protein and/or active fragment and/or derivative thereof.

10 Claims, 12 Drawing Sheets

Specification includes a Sequence Listing.

(56) References Cited

OTHER PUBLICATIONS

Su J.H. et al., Immunohistochemical evidence for apoptosis in Alzheimer's disease. Neuroreport. 5(18):2529-33 (1994).
Eliseeva I.A. et al., Y-box binding protein (YB-1) and its functions / Biochemistry (Mosc). 1:65-132 (2011) RU.
Kohno K. et al., The pleiotropic functions of the Y-boxbinding protein, YB-1 / Bioessays. 35:691-698 (2003).
Skabkin M.A. et al., The major messenger ribonucleoprotein particle protein p50 (YB-1) promotes nucleic acid strand annealing, J. Biol. Chem. 276:44841-44847 (2001).
Ise T. et al., Transcription factor Y-box binding protein 1 binds preferentially to cisplatin-modified DNA and interacts with proliferating cell nuclear antigen, Cancer Res. 59:342-346 (1999).
Chansky H.A. et al., Oncogenic TLS/ERG and EWS/Fli-1 fusion proteins inhibit RNA splicing mediated by YB-1 protein, Cancer Res. 61:3586-3590 (2001).
Skabkin M.A. et al., Structural organization of mRNA complexes with major core mRNP protein YB-1, Nucleic Acids Res. 32: 5621-5635 (2004).
Davydova E.K. et al., Overexpression in COS cells of p50, the major core protein associated with mRNA, results in translation inhibition, Nucleic Acids Res. 25:2911-2916 (1997).
Evdokimova, V. et al., The major mRNA-associated protein YB-1 is a potent 5' cap-dependent mRNA stabilizer, EMBO J. 20:5491-5502 (2001).
Evdokimova, V. et al., Akt-Mediated YB-1 Phosphorylation Activates Translation of Silent mRNA Species, Mol. Cell. Biol. 26(1):277-292 (2006).
Ruzanov P.V. et al., Interaction of the universal mRNA-binding protein, p50, with actin: a possible link between mRNA and microfilaments , J. Cell Sci. 112(20):3487-3496 (1999).
Fotovali A. et al., YB-1 Bridges Neural Stem Cells and Brain Tumor-Initiating Cells via Its Roles in Differentiation and Cell Growth, Cancer Res. 71(16):5569-78 (2011).
Stone J.G. et al., Frontiers in Alzheimer's Disease Therapeutics, Ther Adv Chronic Dis. 2(1):9-23 (2011).
Hanssen L. et al., Y-box binding protein-1 mediates profibrotic effects of calcineurin inhibitors in the kidney, J Immunol. 187(1):298-308 (2011).
Lu Z.H. et al., YB-1 is important for late-stage embryonic development, optimal cellular stress responses, and the prevention of premature senescence, Mol Cell Biol. 25:4625-4637 (2005).
Frye B.C. et al., Y-box protein-1 is actively secreted through a non-classical pathway and acts as an extracellular mitogen, EMBO Rep. 10(7):783-9 (2009).
Rauen T. et al., YB-1 acts as a ligand for Notch-3 receptors and modulates receptor activation, J Biol Chem. 284(39):26928-40 (2009).
Ables J.L. et al., Not(ch) just development: Notch signalling in the adult brain, Nat Rev Neurosci. 12(5):269-83 (2011).
Morris R.G. et al., Selective impairment of learning and blockade of long-term potentiation by an N-methyl-D-asportate receptor antagonist, AP5, Nature, 319:774-776 (1986).
Guryanov S.G. et al., Formation of amyloid-like fibrils by Y-box binding protein 1 (YB-1) is mediated by its cold shock domain and modulated by disordered terminal domains, PLoS One. 7(5):e36969 (2012) Epub May 8, 2012.
Studier F.W., Protein production by auto-induction in high-density shaking cultures, Prot. Exp. Pur. 41:207-234 (2005).
Maciejczyk A. et al., Anticancer research 32: 3177-3184 (2012).
Database GenBank: AAH65571.1, Jun. 23, 2006. found in Internet <URL : https://ncbi.nlm.nih.gov/protein/AAH65571.1.

\* cited by examiner

SEQUENCE LISTING

<160> NUMBER OF SEQ ID NOS: 12

<210> SEQ ID NO 1
<211> LENGTH: 324
<212> TYPE: PRT
<213> ORGANISM: Homo sapiens

<400> SEQUENCE: 1

```
Met Ser Ser Glu Ala Glu Thr Gln Gln Pro Ala Ala Pro Pro Ala
 1               5                  10                  15

Ala Pro Ala Leu Ser Ala Ala Asp Thr Lys Pro Gly Thr Thr Gly Ser
            20                  25                  30

Gly Ala Gly Ser Gly Gly Pro Gly Gly Leu Thr Ser Ala Ala Pro Ala
            35                  40                  45

Gly Gly Asp Lys Lys Val Ile Ala Thr Lys Val Leu Gly Thr Val Lys
         50                  55                  60

Trp Phe Asn Val Arg Asn Gly Tyr Gly Phe Ile Asn Arg Asn Asp Thr
 65                 70                  75                  80

Lys Glu Asp Val Phe Val His Gln Thr Ala Ile Lys Lys Asn Asn Pro
                85                  90                  95
```

```
Arg Lys Tyr Leu Arg Ser Val Gly Asp Gly Glu Thr Val Glu Phe Asp
            100                 105                 110

Val Val Glu Gly Glu Lys Gly Ala Glu Ala Ala Asn Val Thr Gly Pro
        115                 120                 125

Gly Gly Val Pro Val Gln Gly Ser Lys Tyr Ala Ala Asp Arg Asn His
    130                 135                 140

Tyr Arg Arg Tyr Pro Arg Arg Gly Pro Pro Arg Asn Tyr Gln Gln
145                 150                 155                 160

Asn Tyr Gln Asn Ser Glu Ser Gly Lys Asn Glu Gly Ser Glu Ser
                165                 170                 175

Ala Pro Glu Gly Gln Ala Gln Gln Arg Arg Pro Tyr Arg Arg Arg
            180                 185                 190

Phe Pro Pro Tyr Tyr Met Arg Arg Pro Tyr Gly Arg Arg Pro Gln Tyr
        195                 200                 205

Ser Asn Pro Pro Val Gln Gly Glu Val Met Glu Gly Ala Asp Asn Gln
    210                 215                 220

Gly Ala Gly Glu Gln Gly Arg Pro Val Arg Gln Asn Met Tyr Arg Gly
225                 230                 235                 240

Tyr Arg Pro Arg Phe Arg Arg Gly Pro Pro Arg Gln Arg Gln Pro Arg
                245                 250                 255

Glu Asp Gly Asn Glu Glu Asp Lys Glu Asn Gln Gly Asp Glu Thr Gln
            260                 265                 270

Gly Gln Gln Pro Pro Gln Arg Arg Tyr Arg Arg Asn Phe Asn Tyr Arg
        275                 280                 285

Arg Arg Arg Pro Glu Asn Pro Lys Pro Gln Asp Gly Lys Glu Thr Lys
    290                 295                 300

Ala Ala Asp Pro Pro Ala Glu Asn Ser Ser Ala Pro Glu Ala Glu Gln
305                 310                 315                 320

Gly Gly Ala Glu

<210> SEQ ID NO 2
<211> LENGTH: 972
<212> TYPE: DNA
<213> ORGANISM: Homo sapiens

<400> SEQUENCE: 2
atgagcagcg aggccgagac ccagcagccg cccgccgccc cccccgccgc ccccgccctc      60
agcgccgccg acaccaagcc cggcaccacg ggcagcggcg cagggagcgg tggcccgggc     120
ggcctcacat cggcggcgcc tgccggcggg gacaagaagg tcatcgcaac gaaggttttg     180
ggaacagtaa aatggttcaa tgtaaggaac ggatatggtt tcatcaacag gaatgacacc     240
aaggaagatg tatttgtaca ccagactgcc ataaagaaga taaccccag gaagtacctt     300 cgcagtgtag agatggagag gactgtggag tttgatgttg ttgaaggaga aaagggtgcg     360
gaggcagcaa atgttacagg tcctggtgga gttccagtgc aaggcagtaa atatgcagca     420
gaccgtaacc attatagacg atacccacgt cgtagggggtc ctccacgcaa ttaccagcag     480
aattaccaga atagtgagag tgggaaaaag aatgagggat cggagagcgc tcccgaaggc     540
caggcccaac aacgccggcc ctaccgcagg cgaaggttcc caccttacta catgcggaga     600
ccctatgggc gtcgaccaca gtattccaac cctcctgtgc agggagaagt gatggaaggt     660
gctgacaacc agggtgcagg agaacaaggt agaccagtga cagaatat gtatcggggt     720 tatagaccac gattccgcag aggtcctcct cgccaaagcc agcctagaga ggacggcaat     780
```

```
gaagaagaca aggaaaacca aggagatgag acccagggtc agcagccacc tcagcgtcgg    840
taccgccgca acttcaacta ccgacgcaga cgcccagaaa accctaaacc acaagatggc    900
aaagagacaa aagcagaaga tccaccagct gagaattcgt ccgctcccga ggctgagcag    960
ggcggggctg ag                                                        972
```

<210> SEQ ID NO 3
<211> LENGTH: 219
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(219)
<223> OTHER INFORMATION: Fragment YB-1[1-219] of recombinant human
      protein YB-1.

<400> SEQUENCE: 3

```
Met Ser Ser Glu Ala Glu Thr Gln Gln Pro Pro Ala Ala Pro Pro Ala
 1               5                  10                  15

Ala Pro Ala Leu Ser Ala Ala Asp Thr Lys Pro Gly Thr Thr Gly Ser
            20                  25                  30

Gly Ala Gly Ser Gly Gly Pro Gly Gly Leu Thr Ser Ala Ala Pro Ala
        35                  40                  45

Gly Gly Asp Lys Lys Val Ile Ala Thr Lys Val Leu Gly Thr Val Lys
    50                  55                  60

Trp Phe Asn Val Arg Asn Gly Tyr Gly Phe Ile Asn Arg Asn Asp Thr
65                  70                  75                  80

Lys Glu Asp Val Phe Val His Gln Thr Ala Ile Lys Lys Asn Asn Pro
                85                  90                  95

Arg Lys Tyr Leu Arg Ser Val Gly Asp Gly Glu Thr Val Glu Phe Asp
            100                 105                 110

Val Val Glu Gly Glu Lys Gly Ala Glu Ala Ala Asn Val Thr Gly Pro
        115                 120                 125

Gly Gly Val Pro Val Gln Gly Ser Lys Tyr Ala Ala Asp Arg Asn His
    130                 135                 140

Tyr Arg Arg Tyr Pro Arg Arg Gly Pro Pro Arg Asn Tyr Gln Gln
145                 150                 155                 160

Asn Tyr Gln Asn Ser Glu Ser Gly Glu Lys Asn Glu Gly Ser Glu Ser
                165                 170                 175

Ala Pro Glu Gly Gln Ala Gln Gln Arg Arg Pro Tyr Arg Arg Arg
            180                 185                 190

Phe Pro Pro Tyr Tyr Met Arg Arg Pro Tyr Gly Arg Arg Pro Gln Tyr
        195                 200                 205

Ser Asn Pro Pro Val Gln Gly Glu Val Met Glu
    210                 215
```

<210> SEQ ID NO 4
<211> LENGTH: 657
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(657)
<223> OTHER INFORMATION: cDNA that encodes fragment YB-1[1-219] of
      recombinant human protein YB-1

<400> SEQUENCE: 4

```
atgagcagcg aggccgagac ccagcagccg cccgccgccc ccccgccgc cccgccctc      60 agcgccgccg acaccaagcc cggcaccacg ggcagcggcg cagggagcgg tggcccgggc    120
ggcctcacat cggcggcgcc tgccggcggg gacaagaagg tcatcgcaac gaaggttttg    180
ggaacagtaa atggttcaa tgtaaggaac ggatatggtt tcatcaacag gaatgacacc     240
aaggaagatg tatttgtaca ccagactgcc ataaagaaga ataaccccag gaagtacctt    300
cgcagtgtag agatggaga gactgtggag tttgatgttg ttgaaggaga aaagggtgcg     360
gaggcagcaa atgttacagg tcctggtgga gttccagtgc aaggcagtaa atatgcagca    420
gaccgtaacc attatagacg ataccacgt cgtaggggtc ctccacgcaa ttaccagcag     480
aattaccaga atagtgagag tggggaaaag aatgagggat cggagagcgc tcccgaaggc    540
caggcccaac aacgccggcc ctaccgcagg cgaaggttcc caccttacta catgcggaga    600
ccctatgggc gtcgaccaca gtattccaac cctcctgtgc agggagaagt gatggaa       657
```

<210> SEQ ID NO 5
<211> LENGTH: 79
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(79)
<223> OTHER INFORMATION: Fragment YB-1[52-129] of recombinant human protein YB-1

<400> SEQUENCE: 5

```
Met Lys Lys Val Ile Ala Thr Lys Val Leu Gly Thr Val Lys Trp Phe
1               5                   10                  15

Asn Val Arg Asn Gly Tyr Gly Phe Ile Asn Arg Asn Asp Thr Lys Glu
            20                  25                  30

Asp Val Phe Val His Gln Thr Ala Ile Lys Lys Asn Asn Pro Arg Lys
        35                  40                  45

Tyr Leu Arg Ser Val Gly Asp Gly Glu Thr Val Glu Phe Asp Val Val
    50                  55                  60

Glu Gly Glu Lys Gly Ala Glu Ala Ala Asn Val Thr Gly Pro Gly
65                  70                  75
```

<210> SEQ ID NO 6
<211> LENGTH: 237
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(237)
<223> OTHER INFORMATION: cDNA that encodes human fragment YB-1[52-129]

<400> SEQUENCE: 6

```
atgaagaagg tcatcgcaac gaaggttttg ggaacagtaa atggttcaa tgtaaggaac     60 ggatatggtt tcatcaacag gaatgacacc aaggaagatg tatttgtaca ccagactgcc   120
ataaagaaga ataaccccag gaagtaccct cgcagtgtag agatggaga gactgtggag    180 tttgatgttg ttgaaggaga aaagggtgcg gaggcagcaa atgttacagg tcctggt       237
```

<210> SEQ ID NO 7
<211> LENGTH: 324
<212> TYPE: PRT

<213> ORGANISM: Oryctolagus cuniculus

<400> SEQUENCE: 7

Met Ser Ser Glu Ala Glu Thr Gln Gln Pro Ala Ala Pro Pro Ala
1               5                   10                  15

Ala Pro Ala Leu Ser Ala Ala Gly Thr Lys Pro Gly Thr Thr Gly Ser
            20                  25                  30

Gly Ala Gly Ser Gly Gly Pro Gly Leu Thr Ser Ala Ala Pro Ala
        35                  40                  45

Gly Gly Asp Lys Lys Val Ile Ala Thr Lys Val Leu Gly Thr Val Lys
    50                  55                  60

Trp Phe Asn Val Arg Asn Gly Tyr Gly Phe Ile Asn Arg Asn Asp Thr
65              70                  75                  80

Lys Glu Asp Val Phe Val His Gln Thr Ala Ile Lys Lys Asn Asn Pro
                85                  90                  95

Arg Lys Tyr Leu Arg Ser Val Gly Asp Gly Glu Thr Val Glu Phe Asp
            100                 105                 110

Val Val Glu Gly Glu Lys Gly Ala Glu Ala Ala Asn Val Thr Gly Pro
        115                 120                 125

Gly Gly Val Pro Val Gln Gly Ser Lys Tyr Ala Ala Asp Arg Asn His
    130                 135                 140

Tyr Arg Arg Tyr Pro Arg Arg Arg Gly Pro Pro Arg Asn Tyr Gln Gln
145             150                 155                 160

Asn Tyr Gln Asn Ser Glu Ser Gly Glu Lys Asn Glu Gly Ser Glu Ser
                165                 170                 175

Ala Pro Glu Gly Gln Ala Gln Gln Arg Arg Pro Tyr Arg Arg Arg
            180                 185                 190

Phe Pro Pro Tyr Tyr Met Arg Arg Pro Tyr Gly Arg Arg Pro Gln Tyr
            195                 200                 205

Ser Asn Pro Pro Val Gln Gly Glu Val Met Glu Gly Ala Asp Asn Gln
            210                 215                 220

Gly Ala Gly Glu Gln Gly Arg Pro Val Arg Gln Asn Met Tyr Arg Gly
225             230                 235                 240

Tyr Arg Pro Arg Phe Arg Arg Gly Pro Pro Arg Gln Arg Gln Pro Arg
                245                 250                 255

Glu Asp Gly Asn Glu Glu Asp Lys Glu Asn Gln Gly Asp Glu Thr Gln
            260                 265                 270

Gly Gln Gln Pro Pro Gln Arg Arg Tyr Arg Arg Asn Phe Asn Tyr Arg
        275                 280                 285

Arg Arg Arg Pro Asp Asn Pro Lys Pro Gln Asp Gly Lys Glu Thr Lys
    290                 295                 300

Ala Ala Asp Pro Pro Ala Glu Asn Ser Ser Ala Pro Glu Ala Glu Gln
305             310                 315                 320

Gly Gly Ala Glu

<210> SEQ ID NO 8
<211> LENGTH: 972
<212> TYPE: DNA
<213> ORGANISM: Oryctolagus cuniculus

<400> SEQUENCE: 8
atgagcagcg aggccgagac ccagcagccg cccgccgccc ccccgccgc ccccgccctc        60 agcgccgccg aaaccaagcc cggcaccacg ggcagcggcg cagggagcgg tggcccgggc       120
ggcctcacat cggcggcgcc tgccggcggg gacaagaagg tcatcgcaac gaaggttttg       180

```
ggaacagtaa aatggttcaa tgtaaggaac ggatatggtt tcatcaacag gaatgacacc      240
aaggaagatg tatttgtaca ccagactgcc ataaagaaga ataacccag gaagtacctt       300 cgcagtgtag agatggaga gactgtggag tttgatgttg ttgaaggaga aaagggtgcg       360
gaggcagcaa atgttacagg tcctggtgga gttccagtgc aaggcagtaa atatgcagca     420
gaccgtaacc attatagacg atacccacgt cgtagggtc ctccacgcaa ttaccagcag      480
aattaccaga atagtgagag tggggaaaag aatgagggat cggagagcgc tcccgaaggc    540
caggcccaac aacgccggcc ctaccgcagg cgaaggttcc caccttacta catgcggaga    600
ccctatgggc gtcgaccaca gtattccaac cctcctgtgc agggagaagt gatggaaggt     660
gctgacaacc agggtgcagg agaacaaggt agaccagtga dacagaatat gtatcggggt    720
tatagaccac gattccgcag aggtcctcct cgccaaagcc agcctagaga ggacggcaat    780
gaagaagaca aggaaaacca aggagatgag acccagggtc agcagccacc tcagcgtcgg   840
taccgccgca acttcaacta ccgacgcaga cgcccagata accctaaacc acaagatggc    900
aaagagacaa aagcagaaga tccaccagct gagaattcgt ccgctcccga ggctgagcag  960
ggcggggctg ag                                                                             972
```

```
<210> SEQ ID NO 9
<211> LENGTH: 219
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(219)
<223> OTHER INFORMATION: Fragment YB-1[1-219] of recombinant rabbit
      protein YB-1

<400> SEQUENCE: 9
```

```
Met Ser Ser Glu Ala Glu Thr Gln Gln Pro Pro Ala Ala Pro Pro Ala
1               5                   10                  15

Ala Pro Ala Leu Ser Ala Ala Glu Thr Lys Pro Gly Thr Thr Gly Ser
            20                  25                  30

Gly Ala Gly Ser Gly Gly Pro Gly Gly Leu Thr Ser Ala Ala Pro Ala
        35                  40                  45

Gly Gly Asp Lys Lys Val Ile Ala Thr Lys Val Leu Gly Thr Val Lys
    50                  55                  60

Trp Phe Asn Val Arg Asn Gly Tyr Gly Phe Ile Asn Arg Asn Asp Thr
65                  70                  75                  80

Lys Glu Asp Val Phe Val His Gln Thr Ala Ile Lys Lys Asn Asn Pro
                85                  90                  95

Arg Lys Tyr Leu Arg Ser Val Gly Asp Gly Glu Thr Val Glu Phe Asp
            100                 105                 110

Val Val Glu Gly Glu Lys Gly Ala Glu Ala Ala Asn Val Thr Gly Pro
        115                 120                 125

Gly Gly Val Pro Val Gln Gly Ser Lys Tyr Ala Ala Asp Arg Asn His
    130                 135                 140

Tyr Arg Arg Tyr Pro Arg Arg Gly Pro Pro Arg Asn Tyr Gln Gln
145                 150                 155                 160

Asn Tyr Gln Asn Ser Glu Ser Gly Glu Lys Asn Glu Gly Ser Glu Ser
                165                 170                 175

Ala Pro Glu Gly Gln Ala Gln Gln Arg Arg Pro Tyr Arg Arg Arg
            180                 185                 190
```

Phe Pro Pro Tyr Tyr Met Arg Arg Pro Tyr Gly Arg Arg Pro Gln Tyr
            195                 200                 205

Ser Asn Pro Pro Val Gln Gly Glu Val Met Glu
    210                 215

<210> SEQ ID NO 10
<211> LENGTH: 657
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(657)
<223> OTHER INFORMATION: cDNA that encodes rabbit fragment YB-1[1-219].

<400> SEQUENCE: 10
atgagcagcg aggccgagac ccagcagccg cccgccgccc ccccgccgc ccccgccctc    60 agcgccgccg aaaccaagcc cggcaccacg ggcagcggcg cagggagcgg tggcccgggc   120
ggcctcacat cggcggcgcc tgccggcggg acaagaagg tcatcgcaac gaaggttttg   180
ggaacagtaa atggttcaa tgtaaggaac ggatatggtt tcatcaacag gaatgacacc   240
aaggaagatg tatttgtaca ccagactgcc ataaagaaga ataaccccag gaagtacctt   300
cgcagtgtag agatggaga gactgtggag tttgatgttg ttgaaggaga aaagggtgcg   360
gaggcagcaa atgttacagg tcctggtgga gttccagtgc aaggcagtaa atatgcagca   420
gaccgtaacc attatagacg atacccacgt cgtaggggtc ctccacgcaa ttaccagcag   480
aattaccaga atagtgagag tggggaaaag aatgagggat cggagagcgc tcccgaaggc   540
caggcccaac aacgccggcc ctaccgcagg cgaaggttcc caccttacta catgcggaga   600
ccctatgggc gtcgaccaca gtattccaac cctcctgtgc agggagaagt gatggaa     657

<210> SEQ ID NO 11
<211> LENGTH: 79
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(79)
<223> OTHER INFORMATION: Fragment YB-1[52-129] of recombinant rabbit
      protein YB-1

<400> SEQUENCE: 11

Met Lys Lys Val Ile Ala Thr Lys Val Leu Gly Thr Val Lys Trp Phe
1               5                   10                  15

Asn Val Arg Asn Gly Tyr Gly Phe Ile Asn Arg Asn Asp Thr Lys Glu
            20                  25                  30

Asp Val Phe Val His Gln Thr Ala Ile Lys Lys Asn Asn Pro Arg Lys
        35                  40                  45

Tyr Leu Arg Ser Val Gly Asp Gly Glu Thr Val Glu Phe Asp Val Val
    50                  55                  60

Glu Gly Glu Lys Gly Ala Glu Ala Ala Asn Val Thr Gly Pro Gly
65                  70                  75

<210> SEQ ID NO 12
<211> LENGTH: 237
<212> TYPE: DNA
<213> ORGANISM: Artificial Sequence
<220> FEATURE:

<223> OTHER INFORMATION: Synthetic construct
<220> FEATURE:
<221> NAME/KEY: misc_feature
<222> LOCATION: (4)..(237)
<223> OTHER INFORMATION: cDNA that encodes rabbit fragment YB-1[52-129]

<400> SEQUENCE: 12

```
atgaagaagg tcatcgcaac gaaggttttg ggaacagtaa aatggttcaa tgtaaggaac      60
ggatatggtt tcatcaacag gaatgacacc aaggaagatg tatttgtaca ccagactgcc     120
ataaagaaga ataaccccag gaagtacctt cgcagtgtag gagatggaga gactgtggag     180
tttgatgttg ttgaaggaga aaagggtgcg gaggcagcaa atgttacagg tcctggt        237
```

APPLICATION OF YB-1 PROTEIN AND FRAGMENTS THEREOF FOR PREPARING MEDICINAL AGENTS IN TREATING ALZHEIMER'S DISEASE

FIELD OF THE INVENTION

The present invention relates to the field of genetic engineering and medicine. Proposed is a method for treating neurodegenerative diseases and Alzheimer's disease that includes the intranasal administration to a subject of a therapeutically effective amount of the YB-1 protein and/or active fragment and/or derivative thereof.

BACKGROUND OF THE INVENTION

Alzheimer's disease (AD) is a most widespread neurodegenerative pathology that affects one of four people over the age of 75 years. A specific neurodegenerative process developing in the memory-responsible brain structures underlies this disease. In spite of tremendous financial expenditures on research and symptomatic treatment of AD, it still remains incurable and eventually leads to death.

According to the World Health Organization, the prevalence of this disease is expected to increase with increasing total life expectancy in developed countries. Currently, there exist no effective means for AD prevention or essential retardation. Therefore, elucidation of the molecular mechanisms underlying AD development and search for effective treatment for this disease are vitally important problems.

According to clinical and epidemiological studies in representative groups of elderly people in Moscow, 4.5% of them have AD at the age of 60, their number growing with the age and reaching 15% at the age of 80 and beyond (Gavrilova, 2010 [RU]). The present strategy of AD therapy includes the following treatment modes: 1) compensatory (substitutive) therapy aimed to overcome neurotransmitter deficiency; 2) neuroprotective therapy which implies the use of neuroprotective agents and neurotrophic factors; correction of disturbance of free radical-involving events and calcium methabolism; the use of agents decreasing synthesis of [beta]-amyloid or causing its disaggregation, as well as metal-chelating agents; 3) immunotherapy against both [beta]-amyloid itself and the receptors mediating its neurotoxic effect; 4) the use of agents reducing hyperphosphorylation of the tau-protein or decreasing the level of cholesterol; 5) anti-inflammatory treatment; 6) hormonal treatment; 7) behavioral treatment including psychopharmacotherapy for productive psychopathological disorders and psychological correction (training) of cognitive functions (Bachurin et al., 2010 [RU], Stone et al., 2011).

Presently, AD treatment utilizes acetylcholinesterase inhibitors, agonists of muscarinic and nicotinic acetylcholine receptors, the agents promoting synthesis and accumulation of acetylcholine, which compensates deficiency of the acetyl cholinergic system, and neuroprotectors including calcium channel-blocking agents, NMDA-receptor antagonists (memantine), lazaroids (21-amino steroids), enzyme-blocking agents, stable analogs of endogenous neurotrophins and growth factors, peptidergic substances, and drugs based on brain-specific proteins (Gavrilova, 2002 [RU]). However, all these drugs provide only a delay in development of AD that remains incurable and lethal.

There are two forms of AD: sporadic and hereditary, the former being the most widespread and nine times more frequent than the latter. In recent years, more than ten various theories of AD etiology have been put forward. This disease can result from a combination of various factors that eventually lead to similar clinical and morphological pathologies. Basically, AD pathomorphology is represented by intra- and extracellular cerebral amyloidosis, neurofibrillary tangles, decreased synaptic density in the hippocampus, neuron death by apoptosis, and reactive astrogliosis (Bertoni-Freddari et al., 1996; Su et al., 1994). These morphological changes are of a mosaic nature and occur as sequential events in specific brain areas; their development correlates with the severity of cognitive impairment in patients with AD.

As shown by experiments on olfactory bulbectomized (OBX) animals, they develop a number of pathologies typical of AD, namely, (i) impairment of spatial memory; (ii) an increased level of [beta]-amyloid and formation of its plaque-like aggregates in the cerebral cortex, white matter, and hippocampus of guinea pigs whose [beta]-amyloid primary structure is identical to human one; (iii) dysfunction of the acetyl cholinergic system; (iv) neuron death in the AD-afflicted brain structures (the temporal cortex, hippocampus, and serotonin-synthesizing dorsal raphe nucleus of the brainstem); and (v) changes in the peripheral immune system similar to those observed in patients with AD (Bobkova et al., 2001, 2004, 2010 [RU], Bobkova et al., 2005; Nesterova et al., 2008).

Currently, the above is one of the most valid models of sporadic AD. It has been used, for example, to elucidate the effect of the heat shock protein Hsp70 on neurodegeneration. As follows from a variety of data, Hsp70 can produce a protective effect on mouse spatial memory. There exists an invention (WO 2013006076) describing intranasally administered Hsp70 as the means for treatment of neurodegenerative diseases. Along with the method of intranasal administering of Hsp70, the invention provides a therapeutically effective dose of Hsp70 and/or active fragment and/or derivative substance thereof.

Taking into account the difficulties of AD treatment, the list of existing therapeutically active agents should necessarily be extended. The technical result in the focus of the current invention is a method of the treatment of neurodegenerative diseases in mammals using the Y-box binding protein 1 (YB-1), and/or fragments and/or derivative thereof.

SUMMARY OF THE INVENTION

One aspect of the present invention is elaboration of a method of the treatment of neurodegenerative diseases in a subject in need thereof comprising intranasal administering to the subject a therapeutically effective amount of the full-length protein YB-1 and/or active fragment and/or derivative thereof.

Another aspect of the invention is formulating a composition comprising the full-length protein YB-1 and/or active fragment and/or derivative thereof aimed for simultaneous, or individual, or sequential administering in the course of the treatment of a neurodegenerative disease.

In one embodiment, the YB-1 protein used in the method of the invention is a full-length YB-1$_{1\text{-}324}$ protein that has the amino acid sequence typical of a group of amino acid sequences comprising human SEQ ID NO: 1, rabbit SEQ ID NO: 7.

In another embodiment, active fragment of this protein YB-1$_{1\text{-}219}$ that has the amino acid sequence typical of a group of amino acid sequences comprising human SEQ ID NO: 3, rabbit SEQ ID NO: 9 is used.

In another embodiment, active fragment $YB-1_{52-219}$ that has the amino acid sequence typical of a group of amino acid sequences comprising human SEQ ID NO: 5, rabbit SEQ ID NO: 11 is used.

In another embodiment, active fragment $YB-1_{1-219}$ and/or active fragment $YB-1_{52-129}$ in combination with the full-length $YB-1_{1-324}$ are used.

Another aspect of the invention relates to the dosage which may range widely due to extremely low toxicity of YB-1 and fragments thereof and depend on a number of factors such as body weight, sex, and age of the patient.

In one embodiment, the amount of YB-1 protein and/or at least one active fragment thereof and/or their composition administered to a mammal according to the method of the invention is within the range from 0.2 mcg to 1 mg per kg body weight per day. In another embodiment, the amount of YB-1 protein and/or at least one active fragment thereof and/or their composition administered according to the method of the invention is within the range from 0.2 mcg to 100 mcg per kg body weight per day. In yet another embodiment, the amount of YB-1 protein and/or at least one active fragment thereof and/or their composition administered according to the method of the invention is within the range from about 10 mcg to about 100 mcg per kg body weight per day. In a further embodiment, the amount of YB-1 protein and/or at least one active fragment thereof and/or their composition administered according to the method of the invention is within the range from about 100 mcg to about 1 mg per kg body weight per day.

Another aspect of the invention is the daily dose comprising YB-1 protein and/or at least one active fragment thereof and/or their combination administered once a day for a period from 3 weeks to 5 months.

Another aspect of the invention is a composition of YB-1 protein and/or fragments thereof further comprising additional agents which facilitate brain delivery.

Another aspect of the invention is a composition of YB-1 protein and/or fragments thereof further comprising at least one additional therapeutic agent. Non-limiting examples of such additional therapeutic agents include memory enhancement agents, antidepressants, tranquilizers, antipsychotic agents, sleep disorder agents, anti-inflammatory agents, antioxidant agents, cholesterol modulating agents, and antihypertensive agents.

In another embodiment, YB-1 protein and fragments thereof may be administered either as a combined dose or as separate agents; in the latter case, the set of a few agents is to be supplied together with a prescription for their sequential, simultaneous, or individual administering.

In another embodiment, YB-1 protein and fragments thereof is capable of producing a neuroprotective effect on the mammals at various stages of development of the AD-type neurodegeneration.

The therapeutic agents based on YB-1 protein and/or fragments thereof can be used for the treatment of neurodegenerative diseases associated with abnormal protein synthesis such as Alzheimer's disease, Parkinson's disease, Huntington's Chorea, senile dementia, frontotemporal dementia, Creutzfeldt-Jakob disease, multiple sclerosis, cognitive impairment, prion diseases.

BRIEF DESCRIPTION OF THE DRAWINGS

The current invention is illustrated by FIGS. 1-8.

DETAILED DESCRIPTION OF THE INVENTION

Figure 1:
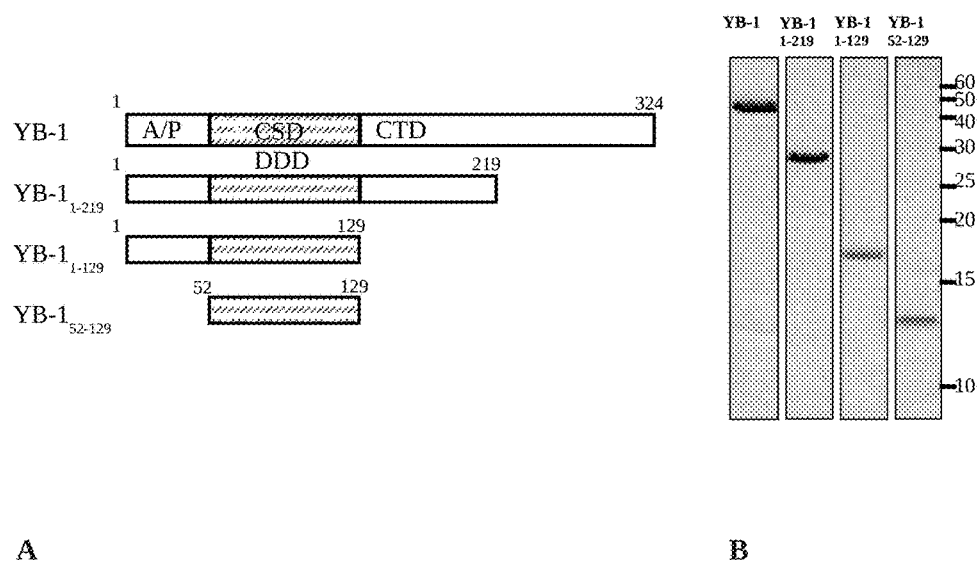
FIG. 1. YB-1 and fragments thereof used in the invention. A, domain structure of $YB-1_{1-324}$ and fragments thereof. B, Electrophoretic analysis of YB-1 and fragments $YB-1_{1-219}$ and $YB-1_{52-129}$ thereof.

The present invention is based on an unexpected observation that a three weeks-long intranasal administration of recombinant YB-1 and/or fragments thereof in OBX mice with spatial memory impairment typical for patients with AD leads to a significant memory improvement.

A search for novel methods of AD treatment highlighted the multifunctional Y-box binding protein 1 (YB-1 or YBX1). Full-length a.a. 324 YB-1 (YB-$1_{1-324}$) is a member of the family of highly conserved proteins with the cold shock domain. The amino acid sequence of human YB-1 differs, for example, from that of rabbit YB-1 only by two synonymous amino acid substitutions (E24D, D293E). YB-1 is a DNA- and RNA-binding protein; it participates in a number of cellular events, including proliferation, differentiation, and stress response (Eliseeva et al., 2011). Through binding to certain nucleotide sequences in promoters of a number of important genes YB-1 exerts positive or negative influence upon transcription of these genes (Kohno et al., 2003). Besides, the elevated affinity of YB-1 for DNA regions with damaged secondary structure implies its involvement in DNA reparation, while its ability to expedite the exchange of complimentary nucleotide sequences in double-stranded DNA suggests its possible participation in DNA recombination (Skabkin et al., 2001; Ise et al., 1999). Also, YB-1 is involved in alternative splicing of mRNA precursors (Chansky et al., 2001), mRNA packaging in the cytoplasm, functional activation and stability of mRNAs, and localization of translatable mRNAs on the actin cytoskeleton (Skabkin et al., 2004; Davydova et al., 1997; Evdokimova et al., 2001; Evdokimova et al., 2006; Ruzanov et al., 1999). There is evidence that YB-1 plays an important role in proliferation activation, maintaining of the stem cell status, and differentiation of neuronal progenitors (Fotovati et al., 2011). Under oxidative stress, accumulated YB-1 up-regulates cell resistance to the stress and prevents premature aging (Hanssen et al., 2011; Lu et al., 2005). Moreover, it has been shown that YB-1 can be secreted from the cell by a non-classical mechanism (Frye et al., 2009) and act as a ligand of the Notch3 receptor, thereby stimulating cell division (Rauen et al., 2009). Importantly, neurodegenerative pathologies, including AD, are often accompanied by neuron loss, oxidative stress, and disturbances in the Notch signaling pathway (Ables et al., 2011). All the above properties of YB-1 characterize this protein as a promising agent to be used for the treatment of neurodegenerative diseases, including AD.

Nevertheless, in spite of reports on YB-1 involvement in cell proliferation and neuron status maintaining, this protein has never been regarded as a potentially useful agent for retardation of the AD-type neurodegeneration, and its solution has never been proposed for intranasal (through nasal passages) injections in order to suppress disturbances in mammal nervous tissue and cerebration.

The effect of intranasally administered YB-1 was revealed in experiments using OBX animals. It appeared that subchronic intranasal injections of full-length YB-$1_{1-324}$ prevented memory loss in OBX mice. A pronounced protective effect also resulted from the use of fragment YB-$1_{1-219}$. The obtained results showed effectiveness of YB-1 and fragment YB-$1_{1-219}$ thereof for the treatment of the AD-type neurodegeneration.

It was found that intranasally administered YB-1 (a rather large protein of 36 kDa) and/or fragments YB-$1_{1-219}$ and YB-$1_{52-129}$ thereof reduced cognitive disturbances developed in OBX mice. Specifically, intranasally administered recombinant YB-1 and/or fragments thereof normalized neuronal density in the temporal cortex, which correlated with a decreased amount of [beta]-amyloid and essentially improved spatial memory.

The method of treatment of a neurodegenerative disease in a subject in need thereof comprises intranasal administering to the subject a therapeutically effective amount of YB-1 protein and/or active fragment and/or derivative thereof.

The present invention is based on the obtained results and relates to the use of full-length YB-$1_{1-324}$ or fragments YB-$1_{1-219}$ and/or YB-$1_{52-129}$ thereof for the treatment of neurodegenerative diseases associated with abnormal protein synthesis and cognitive disturbances. This group of diseases includes Alzheimer's disease, Parkinson's disease, Huntington's Chorea, Lewy Body dementia, frontotemporal dementia, vascular dementia, mild cognitive impairment, mixed dementia, Creutzfeldt-Jakob disease, normal pressure hydrocephalus, Wernicke-Korsakoff syndrome, multiple sclerosis, amyotrophic lateral sclerosis, prion diseases, and different ataxias.

The YB-1 protein used according to the method of the invention is selected from the group of full-length recombinant human and rabbit YB-$1_{1-324}$ proteins which proteins have amino acid sequences corresponding to SEQ ID NO: 1 and SEQ ID NO: 7.

In another embodiment, one, two or more active fragments of YB-1 are used. These fragments are selected from the group of YB-$1_{1-219}$ proteins and the group of YB-$1_{52-129}$ proteins which proteins have amino acid sequences corresponding to human SEQ ID NO: 3, rabbit SEQ ID NO: 9 and human SEQ ID NO: 5, rabbit SEQ ID NO: 11, respectively.

Apart from the above fragments, this group may include other therapeutically active fragments. Polypeptides that are derivatives of YB-1 and fragments thereof may also be used in the methods of the present invention. As compared to YB-1 and fragments thereof, amino acid sequences of these polypeptides additionally contain one or more amino acid deletions and/or insertions and/or substitutions which can take place provided that the resulting polypeptides possess therapeutic activity with respect to neurodegenerative diseases (such therapeutic activity can be tested, e.g., using any of the methods described in the Examples section).

FIG. 1 presents the structure and analysis of YB-1 and fragments thereof used in the invention, where A shows the domain structure of YB-$1_{1-324}$ and fragments thereof and B represents an electrophoretic analysis of YB-1 and fragments thereof.

YB-1 protein and fragments or derivatives thereof may be administered either simultaneously (in a single composition or different compositions) or sequentially; in the latter case, the set of two or more therapeutic compositions is to be supplied as separate doses thereof together with a prescription for their sequential, simultaneous or individual administering.

Expression Systems

Expression systems suitable for production of a recombinant protein or fragments thereof are well known to those skilled in the art of genetic engineering and include, e.g., *E. coli* expression systems (with known vectors), yeast expression systems, and other mammalian expression systems. Non-limiting examples of systems useful for YB-1 production include expression systems described in Example 2 (Guryanov et al, 2012).

Purification of YB-1 and Fragments Thereof

Methods of purification of YB-1 and fragments thereof are well-known in the art. For example, proteins can be purified using affinity chromatography. Non-limiting examples of the purification methods used in the present invention are described in Example 3.

Compositions of the Invention

As indicated above, the pharmaceutical compositions of the invention should comprise a therapeutically effective amount of the YB-1 protein, fragment or derivative of the invention. The optimal therapeutic concentration of YB-1 protein, fragment or derivative in the pharmaceutical compositions of the present invention will necessarily depend upon the activity of the specific YB-1, fragment, or derivative being used, characteristics of the patient (weight, age) and the nature of the neurodegenerative disease for which the agent is being used. In addition, the concentration of the YB-1 protein, fragment or derivative thereof will depend upon whether it is being employed in a preventive or treatment capacity. Further, the stage of a particular disease or disorder, e.g., early vs. late AD, may dictate the optimal concentration of the YB-1 protein, fragment or derivative.

Dosage regimens should be adjusted to provide an optimum activity for a specific disease and patient. Dosages should also be adjusted based on the release rate of the administered formulation (e.g., a nasal spray versus drops). The amount of active compound will generally be chosen to provide effective treatment upon as few administrations as possible, preferably once daily.

An administration regimen of the invention preferably includes a short-term (e.g., weeks to months, e.g., 3 weeks to 5 months for humans) daily treatment, but could also include long-term (e.g., at least 6 months) daily treatment.

As a non-limiting example, the YB-1 protein and/or fragments thereof are suitably present in the composition of the invention in an amount such as to provide a free YB-1 protein concentration from about 0.2 mcg to about 1 mg per kg body weight per day either as a single daily dose or as multiple divided doses during the day.

The proportion of each further component in the nasal composition of the invention may vary depending on the components used. For example, but without being limiting, the amount of nasal carrier may be in the range from 0.1 to 99.9% by weight of the total weight or volume of the composition.

When present, the amount of surfactant may be in the range from about 0.01 to about 10% or higher and preferably about 0.05 to about 10.0% by weight of the total volume or weight of the composition, the amount below the level which may cause irritation of the nasal mucosa.

The amount of delivery enhancing agents may be at least 0.1%, suitably in the range from about 0.5 to 10% of the total weight of the composition. Where the composition is liquid, the enhancing agent may suitably be present in an amount of from 1 to 5% w/v of the total composition.

Preserving agents may be present in an amount of from about 0.002 to 0.02% by weight of the total weight or volume of the composition.

Preferably, the total composition quantity administered at each nasal application comprises from about 0.02 to 0.5 ml, preferably about 0.05 to 0.3 ml, typically about 0.09-0.1 ml. A solid composition may comprise from 1 to 3 mg carrier per dosage, more particularly 4 to 20 mg.

In addition to protein YB-1 and fragments thereof with additives and/or agents, a composition of the invention may contain therapeutic ingredients (or active compounds). Examples of suitable additional therapeutic ingredients are given below.

Drying and Lyophilization

To preserve biological activities of a nasal composition of the invention, it should rather be prepared by lyophilization. A mixture of the YB-1 protein and fragments thereof should preferably be lyophilized together with other ingredients of the composition.

A homogeneous solution, preferably aqueous, containing the YB-1 protein, fragment or derivative of the invention and optionally containing further ingredients, additives and/or agents as discussed above, is prepared and then submitted to lyophilization in analogy with known lyophilization or drying procedures. The resulting powder may then be dissolved in a liquid immediately before administration. The lyophilized product can be used to reconstitute nasal drops, gel or spray. Alternatively, lyophilized powder containing the YB-1 protein and/or fragment thereof may be mixed with further ingredients, additives and/or agents as discussed above.

The activity or physical stability of YB-1 protein and fragments thereof in aqueous solutions or lyophilized preparations can be enhanced by various additives such as, e.g., polyols (including sugars, e.g., sucrose and Ficoll 70]), amino acids, and various salts.

For example, microparticles of YB-1 protein and fragments thereof can be prepared by simply lyophilizing or spray drying a solution containing various stabilizing additives described above. A wide non-limiting range of suitable methods and anti-aggregation agents are available for incorporation within the compositions of the invention such as disclosed in WO2013006076.

Administration

The YB-1 protein (fragment or derivative)-containing pharmaceutical compositions of the present invention are administered intranasally. Such compositions can be administered intranasally as a powdered or liquid spray, nose drops, a gel or ointment, through a tube or catheter, e.g., by syringe, or using a pledget contacted with the nasal mucosa.

The YB-1 protein-containing compositions of the invention can be simple aqueous (e.g., saline) solutions. Alternatively, they can contain various additional ingredients which enhance stability and/or nasal delivery of YB-1 protein and fragments thereof. Such additional ingredients are well known in the art (see WO2013006076). Non-limiting examples of useful additional ingredients for enhancing nasal delivery include, e.g., (a) aggregation inhibitory agents (e.g., polyethylene glycol, dextran, diethylaminoethyl dextran, and carboxy methyl cellulose), (b) charge modifying agents, (c) pH control agents, (d) modulatory agents of epithelial junction physiology, such as, e.g., vasodilator agents, (e) selective transport-enhancing agents (e.g., transmembrane transport), and (f) agents stabilizing protein delivery. Non-limiting examples of membrane penetration-enhancing agents useful in the YB-1 protein and/or fragments thereof-containing compositions of the invention include, e.g., (i) a surfactant (e.g., Tween 80, Poloxamer 188, polysorbates), (ii) a salt or salt derivative (e.g., unsaturated cyclic ureas and Transcutol), (iii) a phospholipid or fatty acid additive mixed with liposomes, (iv) an ethanol, (v) an enamine, (vi) a nitric oxide donor compound (e.g., S-nitroso-N-acetyl-DL-penicillamine, NOR1, NOR4, which are preferably co-administered with an NO scavenger such as doclofenac sodium), (vii) a long-chain amphipathic molecule (e.g., deacylmethyl sulfoxide, sodium lauryl sulfate, oleic acid), (viii) a small hydrophobic penetration enhancer, (ix) sodium salicylate or a salicylic acid derivative (e.g., acetyl salicylate, choline salicylate, salicylamide, etc.), (x) a glycerol ester of acetoacetic acid, (xi) a cyclodextrin or [beta]-cyclodextrin derivative, (xii) a medium-chain fatty acid including mono- and diglycerides (e.g., sodium caprate—extracts of coconut oil, Capmul), (xiii) a chelating agent (e.g., citric acid, salicylates), (xiv) an amino acid or salt thereof (e.g. monoaminocarboxlic acids such as glycine, alanine, phenylalanine, proline, hydroxyproline, etc.; hydroxyamino acids such as serine; amino acids such as aspartic acid, glutamic acid, etc; and basic amino acids such as lysine etc., inclusive of their alkali metal or alkaline earth metal salts), (xv) an N-acetylamino acid or salt thereof, (xvi) an enzyme degradative to a selected membrane component, (xvii) an inhibitor of fatty acid synthesis, (xviii) an inhibitor of cholesterol synthesis, (xix) cationic polymers, or any combination thereof. The membrane penetration-enhancing agent can be also selected from small hydrophilic molecules, including, but not limited to, dimethyl sulfoxide (DMSO), dimethylformamide, ethanol, propylene glycol, and the 2-pyrrolidones. Additional membrane penetration enhancers include emulsifiers (e.g. sodium oleyl phosphate, sodium lauryl phosphate, sodium lauryl sulfate, sodium myristyl sulfate, polyoxyethylene alkyl ethers, etc.). caproic acid, lactic acid, malic acid and citric acid and salts thereof, pyrrolidonecarboxylic acids, alkylpyrrolidonecarboxylic acid esters, N-alkylpyrrolidones, prolineacyl esters, and the like; glycerol esters of acetoacetic acid (e.g., glyceryl-1,3-diacetoacetate or 1,2-isopropylideneglycerine-3-acetoacetate) and triglycerides (e.g., amylodextrin, Estaram 299, Miglyol 810); cyclodextrins and [beta]-cyclodextrin derivatives (e.g., 2-hydroxypropyl-[beta]-cyclodextrin and heptakis (2,6-di-O-methyl-[beta]-cyclodextrin)) which can be optionally conjugated with YB-1 and further optionally formulated in an oleaginous base; and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts), as well as other penetration-promoting agents that are physiologically compatible for intranasal delivery (see WO2013006076).

Non-limiting examples of useful absorption enhancers include, e.g., surfactants, glycosides, cyclodextrin and glycols. Non-limiting examples of useful bioadhesive agents include, e.g., carbopol, cellulose agents, starch, dextran, and chitosan.

Delivery

The compositions of the invention may further comprise agents which facilitate brain delivery. Non-limiting examples of such useful agents include, e.g., (a) nanocarriers (e.g., nanoparticles coated with transferrin), (b) lipophilic micelles and liposomes (e.g., liposomes coated with targeting molecules such as antibodies, Trojan Horses Liposomes), (c) antibodies (e.g., antibodies against transferrin receptor), (d) insulin receptors, (e) chimeric peptides, etc.

These nasal delivery-enhancing agents may be admixed, alone or together, with other composition ingredients and with the YB-1 protein and/or fragments thereof. For nasal delivery-enhancing agents to be of value within the invention, it is generally desired that any significant changes in permeability of the mucosa be reversible within a time frame appropriate to the desired duration of drug delivery. Furthermore, there should be no substantial, cumulative toxicity, nor any permanent deleterious changes induced in the barrier properties of the nasal mucosa with long term use.

Delivery Device

The present invention encompasses any delivery device that is suitable for nasal administration of the compositions of the invention. Preferably, such means administers a metered dosage of the composition. Non-limiting examples of useful intranasal delivery devices include, e.g., catheters, droppers, unit-dose containers, compressed air nebulizers, metered-dose inhalers, etc.

For administration of a liquid in drop form, compositions of the invention can be placed in a container provided with a conventional dropper/closure device, preferably delivering a substantially fixed volume of composition/drop.

A dry powder may be readily dispersed in an inhalation device.

The delivery device (or its packaging) can be optionally provided with a bar-coded label disclosing the drug producer, date of issue, and other important information, and/or with instructions for use indicating that the composition should be used intranasally.

Preventive Measures and Treatment

In the treatment methods of the invention, intranasal YB-1 protein and fragments or derivatives thereof can be administered in combination with various other preparations which can be useful for neurodegenerative diseases. For example, YB-1 protein and fragments or derivatives thereof can be administered in combination with the following:

(a) acetylcholinesterase inhibitors, e.g., donepezil (Aricept™), galantamine hydrobromide (Reminyl), rivastigmine (Exelon) and ipidacrine (neuromidin);

(b) memory enhancement agents that reduce glutamate excitotoxicity (Akatinol Memantine™);

(c) antidepressants (Paroxetine™). Typically, a selective serotonin reuptake inhibitors (trazodone, buspirone), and tricyclic antidepressants with minimal M-anticholinergic action (desipramine and nortriptyline) are used;

(d) anxiolytic agents (thioridazine), antipsychotics (haloperidol) or benzodiazepines (lorazepam);

(e) a sleep disorder agent (diphenhydramine);

(f) anti-inflammatory agents (nonsteroidal ibuprofen, diclofenac, etc.);

(g) antioxidant agents (vitamin E, or a standardized extract of the leaves of *Ginkgo biloba* (EGb 761) contained in the formulation Memoplant);

(h) cholesterol modulating agents e.g., agents which reduce cholesterol, statins (atorvastatin, pravastatin, simvastatin, lovastatin, and fluvastatin), and antagonists of histamine (H2) receptors (Dimebon) (see WO2013006076).

EXAMPLES

Below, the present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. Genetic Construct for Expression of YB-1 Protein and Fragments Thereof Synthesis of recombinant YB-1 was induced in *E. coli* BL21(DE3) cells transformed by the plasmid pET-3-1-YB-1 (p50) which provides IPTG-induced biosynthesis of a recombinant protein.

Example 2. Expression of YB-1 Protein and Fragments Thereof

*E. coli* BL21(DE3) cells were transformed using a genetic construct encoding the needed polypeptide. The transformed cells were cultivated in the medium for autoinduction ZYP-5052 (Studier, 2005) containing 1% tryptone, 0.5% yeast extract, 50 mM Na$_2$HPO$_4$, 50 mM KH$_2$PO$_4$, 25 mM (NH$_4$)$_2$SO$_4$, 2 mM MgSO$_4$, 0.5% glycerol, 0.05% glucose, and 0.2% lactose in a shaker at 37° C. for 16-18 h, followed by centrifugation at 6,000 rpm (rotor JA-10, Beckman, USA) for 10 min. In the case of YB-1 or YB-1$_{1-219}$, the cells were suspended in buffer containing 20 mM Tris-HCl, pH 7.4, with 0.5 mM phenylmethylsulfonylfluoride protease inhibitor and 2M NaCl for dissociation of the target proteins from their complex with ribosomes; in the case of YB-1$_{1-219}$, the buffer used was 50 mM MES-KOH, pH 6.0, with 0.5 mM phenylmethylsulfonylfluoride and 150 mM NaCl; in the case of YB-1$_{52-129}$, the buffer used was 20 mM Hepes-KOH, pH 7.4, with 0.5 mM phenylmethylsulfonylfluoride and 150 mM KCl. The buffer volume was 100 ml per 20 g of cells. Next, the cells were disintegrated for 3 min using an ultrasonic disintegrator UZDN-2T at 44 kHz, 15 mA, followed by centrifugation (rotor JA-14, Beckman, USA) at 8,000 rpm for 20 min to remove cell debris. The resulting supernatant was re-centrifuged at 30,000 rpm for 3 h to remove ribosomes.

Example 3. Purification of YB-1 and Fragments Thereof

To purify YB-1, ribosome-free supernatant was diluted with buffer 20 mM Tris-HCl, pH 7.4, and applied onto a 10 ml heparin-Sepharose column (GE Healthcare, Sweden) equilibrated with buffer 20 mM Tris-HCl, pH 7.4, 500 mM NaCl. The column was washed with five volumes of the same buffer, and in the case of YB-1, additionally with three volumes of buffer 20 mM Tris-HCl, pH 7.4, 750 mM NaCl. Proteins were eluted with buffer 20 mM Tris-HCl, pH 7.4, 2M NaCl, collected as 2 ml fractions and analyzed electophoretically. Fractions with the maximal protein content were combined, concentrated using an Amicon® Ultra-15 (Millipore, France), diluted 3-fold with buffer 20 mM Hepes-KOH, pH 7.4, and applied onto a 1.7 ml MonoS 4.6/100 PE (GE Healthcare) column equilibrated with buffer 20 mM Hepes-KOH, pH 7.4, 0.5M KCl. The protein was eluted by a gradient of 0.5-2M KCl in buffer 20 mM Hepes-KOH, pH 7.4, and subjected to final purification by gel filtration on a Superose 12 10/300 GL (GE Healthcare) column in buffer 20 mM Hepes-KOH, pH 7.4, 1M KCl. Fractions with pure protein were concentrated and dialyzed against 500 mM potassium-phosphate buffer, pH 7.4 (for YB-1) or 20 mM Hepes-KOH, pH 7.4, 150 mM KCl (for YB-1$_{1-219}$).

To purify YB-1$_{1-219}$, ribosome-free supernatant was supplemented with (NH$_4$)$_2$SO$_4$ up to 60% saturation and centrifuged (rotor JA-14) at 8,000 rpm. The pellet was suspended in 50 mM MES-KOH, pH 6.0, 40%-saturated (NH$_4$)$_2$SO$_4$ and applied onto a 50 ml phenyl-Sepharose column (GE-Healthcare) equilibrated with the same buffer. The proteins were eluted by a gradient of 40-0% (NH$_4$)$_2$SO$_4$ in buffer 50 mM MES-KOH, pH 6.0, collected as 2 ml fractions and analyzed electophoretically. Fractions with the maximal protein content were combined, dialyzed against 20 mM MES-KOH, pH 6.0, 50 mM KCl, and applied on a MonoS 4.6/100 PE (GE Healthcare) column equilibrated with the same buffer. The protein was eluted by a gradient of 50-500 mM KCl in buffer 20 mM MES-KOH, pH 6.0; fractions containing the most purified protein were concentrated and dialyzed against 20 mM Hepes-KOH, pH 7.4, 200 mM KCl.

To purify YB-1$_{52-219}$, ribosome-free supernatant was 3-fold diluted with buffer 20 mM Hepes-KOH, pH 7.4, and applied onto a sulfopropyl-Sepharose column equilibrated with 20 mM Hepes-KOH, pH 7.4, 50 mM KCl; proteins were eluted by a gradient of 50-400 mM KCl in buffer 20 mM Hepes-KOH, pH 7.4. Fractions with maximal protein content were combined, mixed with the equal volume of 1M potassium-phosphate buffer, pH 7.4, and applied onto a phenyl-Sepharose column equilibrated with 500 mM potassium-phosphate buffer, pH 7.4. Proteins were eluted by a gradient of 500-0 mM potassium-phosphate buffer; fractions with the maximal protein content were combined, dialyzed against 50 mM potassium-phosphate buffer, pH 7.4, and applied onto a MonoS 4.6/100 PE column (GE Healthcare). Then, proteins were eluted by a gradient of 50-500 mM potassium-phosphate buffer, fractions with the most purified protein were combined, concentrated, and dialyzed against 50 mM potassium-phosphate buffer, pH 7.4.

Figure 4A:
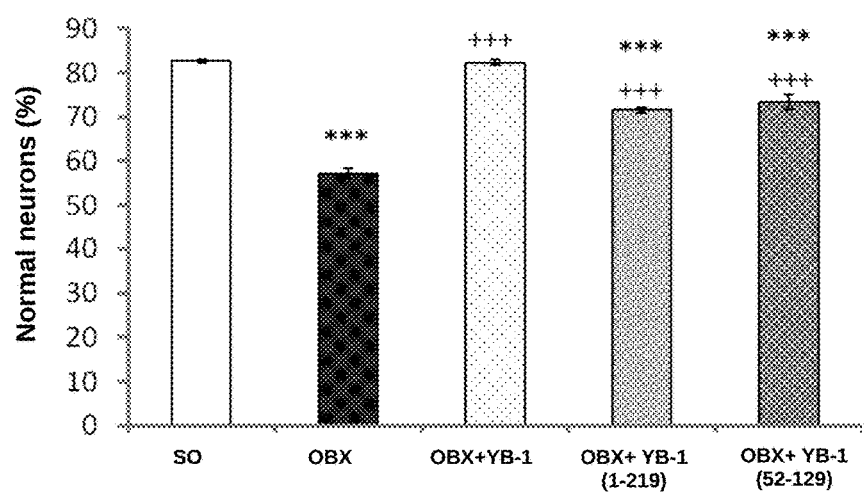
FIG. 4. The effect of intranasally administered YB-1 and fragments $YB-1_{1-219}$ and $YB-1_{52-129}$ thereof on the morphofunctional state of neurons in the temporal cortex of OBX mice. A, percentage of morphologically normal cells by the total number of analyzed cells; B, C, D, percentage of cells with pathologies of pyknosis, cytolysis, and vacuolization type, respectively; E, neuronal density. Significant differences relative to sham-operated (SO) mice are indicated by asterisks (*), while those relative to OBX mice are daggered ($^+$): * or $^{+++}<0.001$;  or $^{++}<0.01$; * or $^+<0.05$.
Figure 4B:
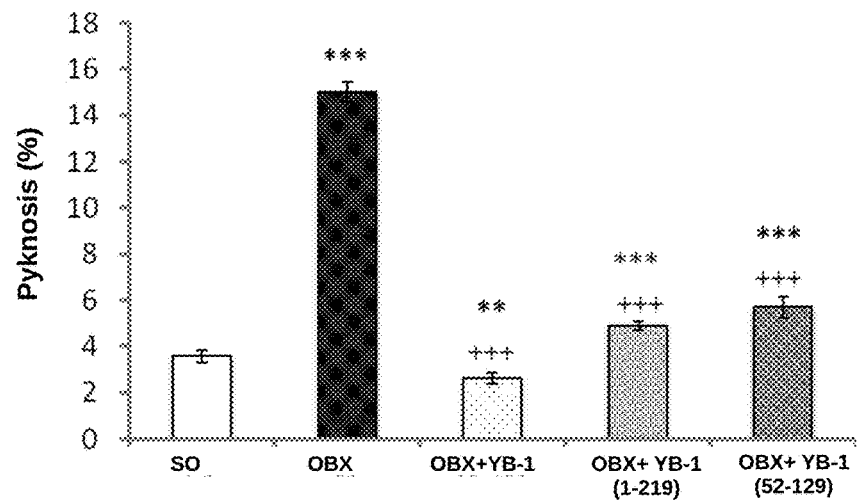
Figure 4C:
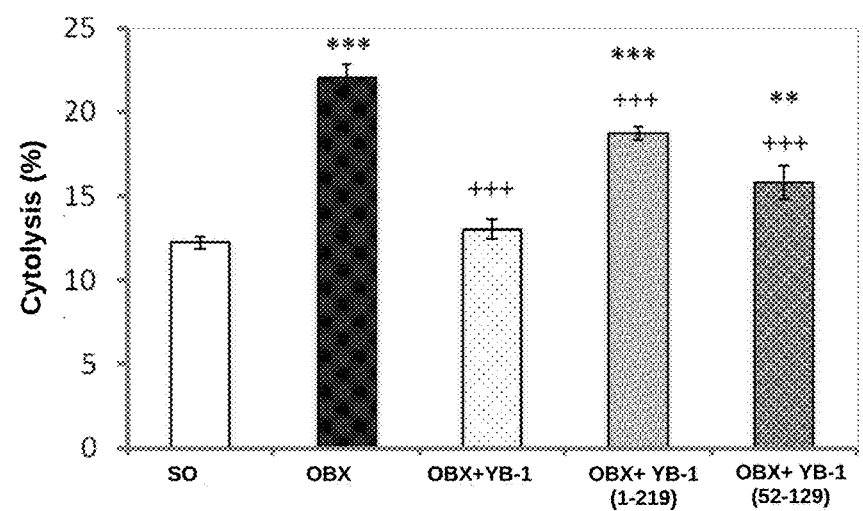
Figure 4D:
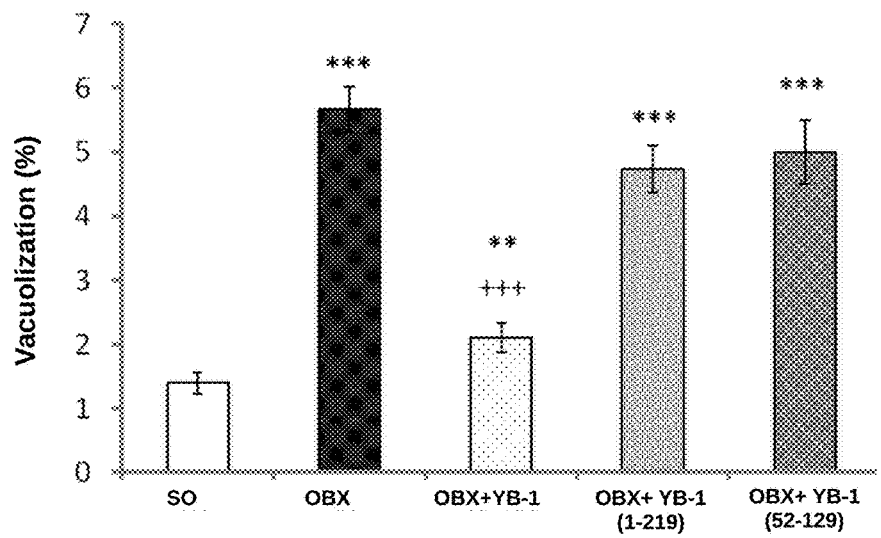
Figure 4E:
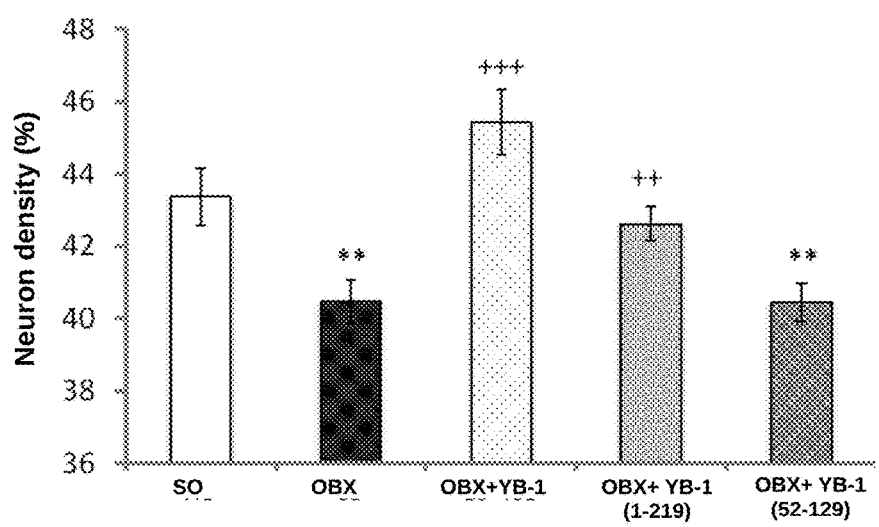
Figure 5A:
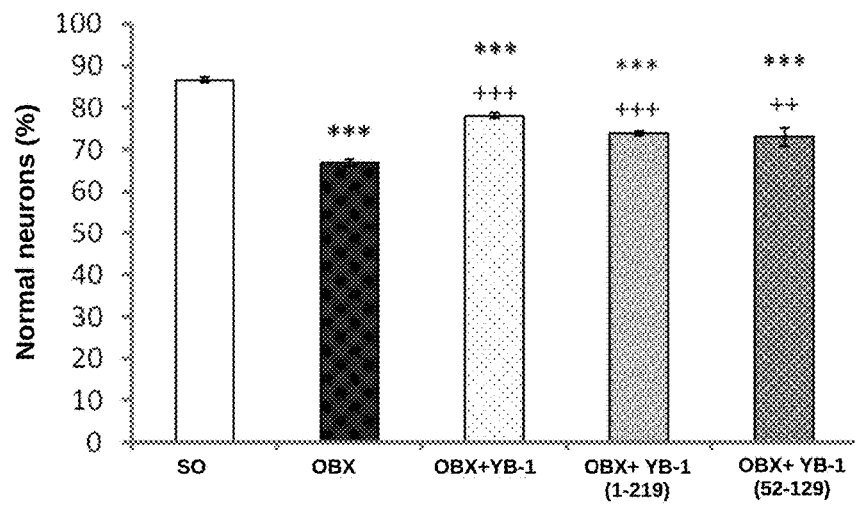
FIG. 5. The effect of intranasally administered YB-1 and fragments $YB-1_{1-219}$ and $YB-1_{52-129}$ thereof on the morphofunctional state of neurons in the CA1 and CA2 areas of the OBX mice hippocampus. A, percentage of normal cells by the total number of analyzed cells; B, C, D, percentage of cells with pathologies of pyknosis, cytolysis, and vacuolization type, respectively; E, neuronal density. Significant differences relative to SO mice are indicated by asterisks (*), while those relative to OBX mice are daggered ($^+$): * or $^{+++}<0.001$;  or $^{++}<0.01$; * or $^+<0.05$.
Figure 5B:
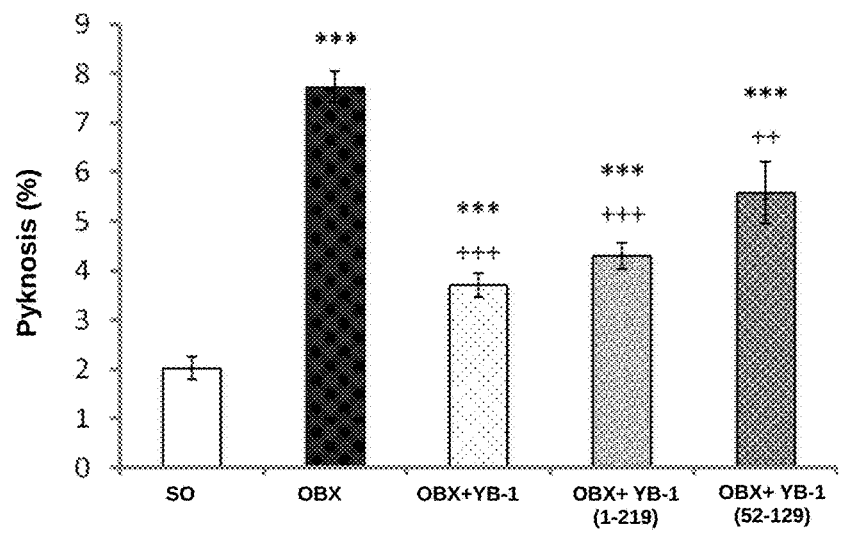
Figure 5C:
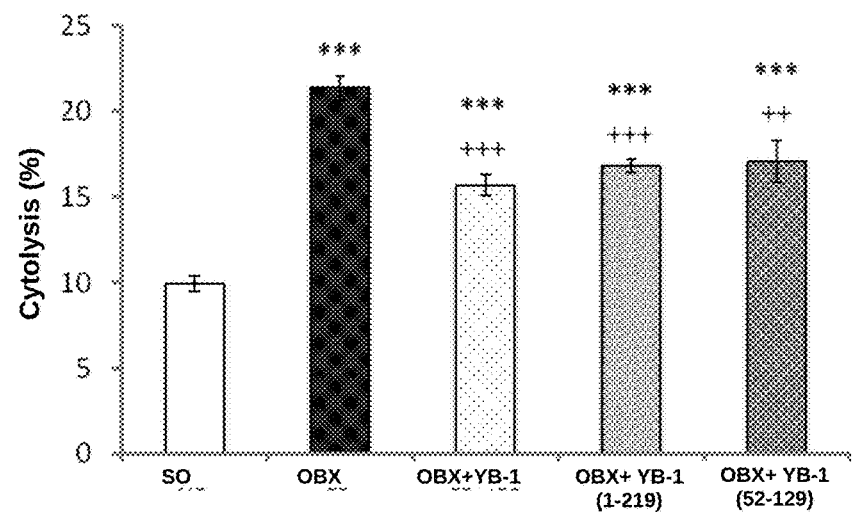
Figure 5D:
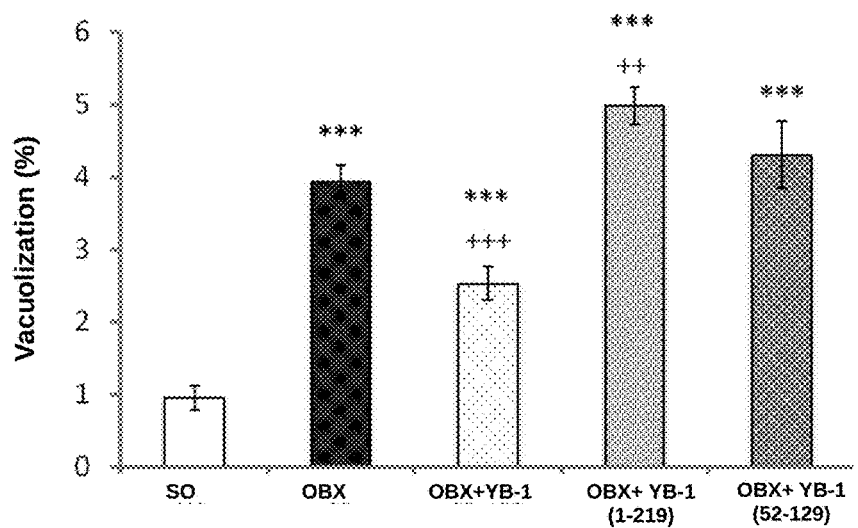
Figure 5E:
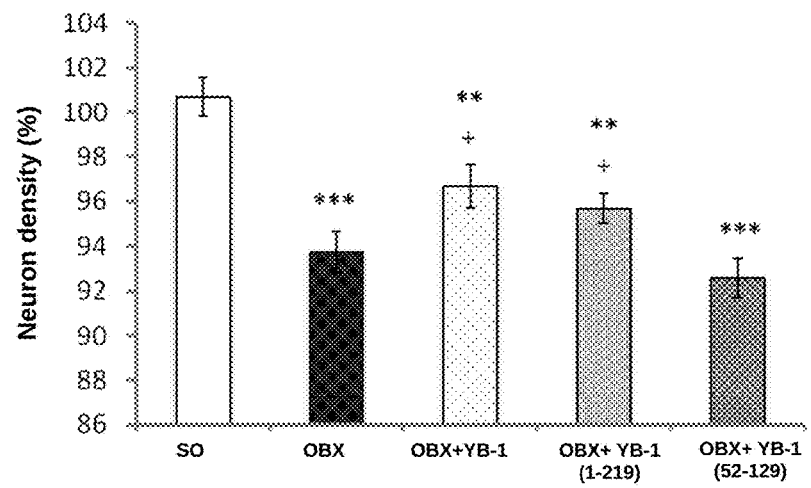
Figure 6A:
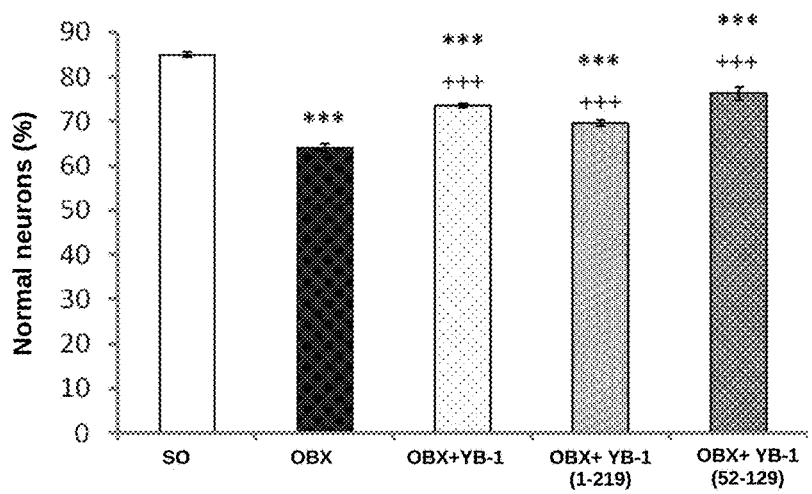
FIG. 6. The effect of intranasally administered YB-1 and fragments $YB-1_{1-219}$ and $YB-1_{52-129}$ thereof on the morphofunctional state of neurons in the CA3 and CA4 areas of the OBX mice hippocampus. A, percentage of normal cells by the total number of analyzed cells; B, C, D, percentage of cells with pathologies of pyknosis, cytolysis, and vacuolization type, respectively; E, neuronal density. Significant differences relative to SO mice are indicated by asterisks (*), while those relative to OBX mice are daggered ($^+$): * or $^{+++}<0.001$;  or $^{++}<0.01$; * or $^+<0.05$.
Figure 6B:
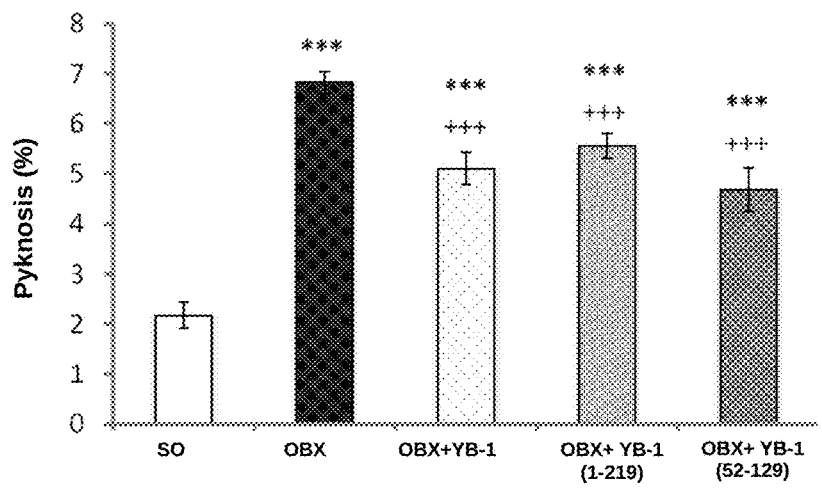
Figure 6C:
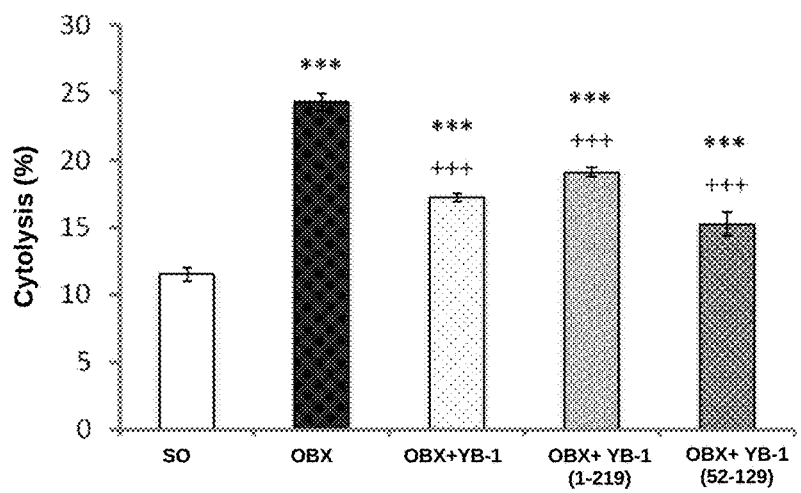
Figure 6E:
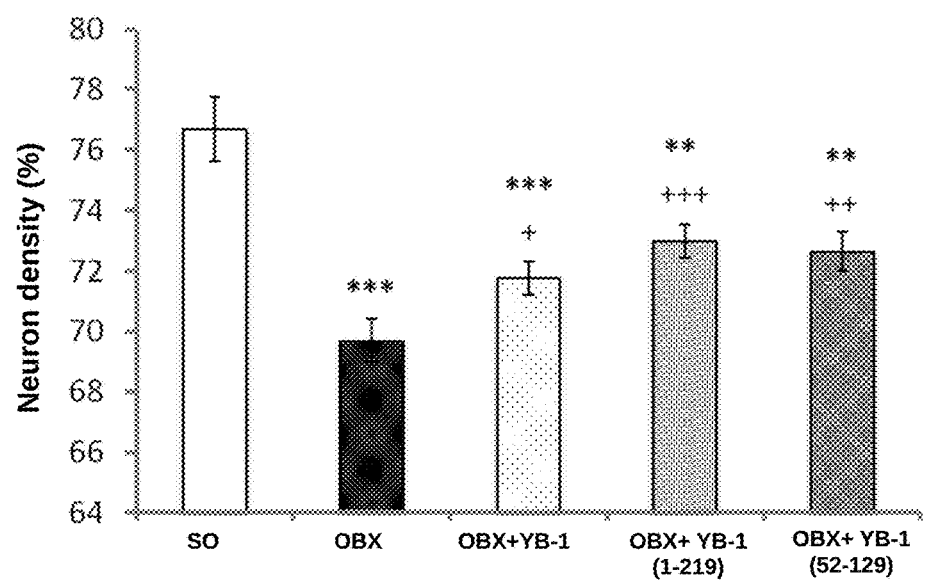

The purity of proteins was analyzed PAAG-electrophoretically (FIG. 4B). The proteins were stored at −80° C. Protein concentration in the preparations was determined from absorbance at 280 nm with the assumption that a solution with an optical density of 1 AU contains 1.37, 1.13, 1.59 or 1.06 mg/ml of YB-1, YB-1$_{1-219}$, YB-1$_{1-219}$, or YB-1$_{52-129}$, respectively. For any of these, the OD$_2$/OD$_{260}$ ratio was about 2, which testifies to the absence of nucleic acids from the preparations.

Example 4. Tests and Analysis of Effectiveness of Compositions Based on YB-1 and/or Fragments Thereof Adult NMRI mice (males) weighing 25-30 g were used in all experiments aimed to determine effectiveness of compositions based on YB-1 and/or fragments thereof. The animals were housed in groups of 5-7 per cage in a climate-controlled room (22-23° C.) with a natural light/dark cycle and free access to water and food.

During a sterile operation for the removal of olfactory bulbs (olfactory bulbectomy) 3-months-old mice were anaesthetized with Nembutal (40 mg/kg, i.p.) and 0.5% Novocaine for local anaesthesia of the scalp. Both olfactory bulbs were aspirated through a burr hole. Sham-operated (SO) mice underwent the same procedure, except olfactory bulb ablation, and served as a control.

Two weeks after the bulbectomy, mice were intranasally injected (using a micropipette) with 4 mcl solution of 1.6 mcg/mcl full-length YB-1 (YB-1$_{1-324}$) or fragment YB-1$_{1-219}$ or YB-1$_{52-219}$. The compositions were administered daily for three weeks (two weeks before and one during the training period.).

Mice were trained to develop a navigational reflex of finding the save platform in the Morris water maze (Morris et al., 1986). In experiments, a plastic circular swimming tank 80 cm in diameter filled with water (23° C.) to a depth of 30 cm was operationally (mentally) divided into four equal sectors one of which, the target sector, contained a hidden save platform at a depth of 0.5 cm. The platform was 5 cm in diameter and invisible to swimming animals in milk-whitened water.

Mice with good swimming habits and low latency to find the save platform were used in experiments. A 5-day training period included four trials daily and was aimed to develop in mice a less than 10 s latency in finding the save platform. The training period was followed by spatial memory tests implying the absence of the save platform for 1 min. The spatial memory was evaluated using two parameters: the time spent by mice in each sector and frequency of visiting each sector.

The next day after memory tests the experimental mice were perfused intracardially with 0.1M phosphate buffer (pH 7.4) under terminal anaesthesia with Nembutal (60 mg/kg, i.p.). Brains were rapidly removed, verified on the extent of the lesion, and divided into hemispheres. Individuals showing a partial lesion and/or any damage of the frontal neocortex were excluded from histological and biochemical analyses, and their results were excluded from behavioral studies. Specimens of the cortex and hippocampus tissue from the left hemisphere were frozen at −70° C. and stored for subsequent DOT and ELISA analyses of the [beta]-amyloid level. The right hemisphere was fixed in 4% phosphate-buffered paraformaldehyde at 4° C. for 48 h before storage in 30% sucrose. Twenty sections of the hemisphere were cut in the coronal plane on a cryostat and stored in ethylene glycol-based cryoprotectant at −20° C. until histological analysis.

To investigate morphological and functional states of neurons from the temporal cortex and hippocampus, the sections were subjected to Nissl staining with Cresyl Violet acetate («Sigma») and examined with an optical microscope Nikon Eclipse E200. The shape and size of the cells, as well as the intensity of staining, represent major morphological details taken into consideration in this analysis. Sections were viewed at a magnification of 20× or 40×, and digitized images were captured using a DXM 1 200 camera mounted on the microscope. Only neurons with well defined cellular contour, nucleus and nucleoli were taken into account.

In order to evaluate the morpho-physiological state of neurons in the area studied, 1000 cells were analyzed in each animal (10 view fields, 40× objective, 10× eyepiece). Comparative studies of cellular compositions of the temporal cortex and the CA1 and CA3 hippocampal areas (1 000 cells for each structure in each mouse were counted) were performed using a digitizer computer system PDP-12 (Germany). Functional neurons and neurons with distinct pathologic changes (cytolysis, pyknosis, and vacuolization) were counted. The cell density was determined in 1 mm$^2$. To measure neuronal density in different brain structures of test mice, an eyepiece with standard object-micrometer was used. The cell number was determined within ten squares of the net, in the area equal to 0.036 mm$^2$ (×40 objective). Density measurements were performed in ten microscopic views. The data were statistically treated using "Statistica 06" program. Comparisons were performed using a two-tailed Student's t-test. The differences were considered to be significant at $p<0.05$.

For biochemical analysis, the brain specimens from test animals were prepared as follows: 200-270 mg of the brain tissue (the cortex and hippocampus) was homogenized in 0.5 ml of 70% formic acid, maintained for 1 h, centrifuged at 100,000 g for 40 min, then the supernatant fluid was evaporated on a rotor evaporator to the minimum volume, supplemented with 1 ml H$_2$O, and the solution was neutralized to pH 7.4 with NaOH and lyophilized.

For immunological analysis, a nitrocellulose membrane was treated with 4% phosphate-buffered (PBS) ovalbumin for 1 min and then with 2.5% glutaraldehyde for 10 min. The brain tissue was applied onto the membrane in 1 mcl spots, and the membrane was further kept for 1 h in 2.5% PBS ovalbumine supplemented with 0.1% sodium azide. Each spot of brain tissue was then supplemented with mouse monoclonal anti-[beta]-amyloid antibodies 4G8 (dilution 1:1000) and incubated for 2 days. Thereafter, the membrane was washed using PBS with 1M NaCl, PBS with 0.05% detergent Tween 20, PBS with 4% ovalbumin, and PBS with 0.1% sodium azide. Then horse antibodies to mouse IgG (dilution 1:3500) was applied followed by 1 h incubation, and membrane washing was performed again. Next, after application of monoclonal antibodies to biotin conjugated with peroxidase (dilution 1:4000), the membrane was treated with a solution of 0.05% hydrogen peroxide and 0.05% o-phenylenediamine in 0.05 Na-citrate buffer, pH 4.5. The staining reaction was stopped by addition of 12.5% sulfuric acid.

For [beta]-amyloid (1-40) detection by the linked immunosorbent assay (ELISA), a number of brain specimens were prepared as follows. Frozen samples of the cortex and hippocampus (stored at −80° C.) were weighted, thawed and homogenized in 2% CHAPS solution, 20 mM Tris-Cl (pH 7.7), with protease inhibitors (10 mcg/ml leupeptin, 10 mcg/ml aprotinin and 10 mcg/ml AEBSF) present in volumes calculated individually for each specimen (4 ml solution per 1 g tissue). The homogenates were centrifuged at 21,000 g at 4° C. for 30 min. The supernatants from the centrifugation were stored frozen at −80° C., and thawed immediately before use in the ELISA. Some other brain specimens were homogenized in 5M guanidine-HCl, 50 mM Tris-HCl (pH 8.0) the volume of which was calculated individually for each specimen (8 mcl solution per 1 mcg tissue). The specimens were mixed for 3-4 h at room temperature and diluted with BSAT-DPBS buffer (5% BSA, 0.03% Tween-20), followed by centrifugation at 21,000 g at 4° C. for 30 min and collection of the supernatant. The detection of [beta] amyloid (1-40) by ELISA was performed according to the manufacturer's instruction to ELISA kit mouse A[beta]40 («Invitrogen»). The optical density was measured at [lambda]=450 nm using an IFA reader («Biorad»).

To assess whether the YB-1 protein can overcome the blood-brain barrier and enter brain structures, the method of protein conjugation with fluorescent cyanine dye Cy3 displaying maximal absorbance at 550 nm and irradiation at 570 nm was used. For the conjugation reaction, 1 mcg of Cy3 was taken per 100 mcl of aqueous YB-1 solution.

The conjugated protein was intranasally administered to OBX and SO mice. Two hours after that the animals' brains were perfused and removed, and brain slices were examined using a confocal microscope HE654.

To assess whether the YB-1 protein can permeate through the cell membrane, the method of protein conjugation with fluorescent dye Cy3 was used.

Transplantable eukaryotic HeLa cells cultivated in normal conditions (10% serum) were incubated in serum-free mixture either with the Cy3-conjugated YB-1 (2.5 mcg/ml) (YB-1-Cy3) or solely with Cy3 for 2 h. After incubation the cells were treated with tripsin, washed with PBS, and either immediately used for preparation of cell smears or applied to wells of another microplate for further growing in normal conditions for 4-6 h. The cells were methanol-fixed, and their nuclear structures were DAPI-stained. The resulting specimens were examined under a confocal microscope Leica TCS SPE.

This is how a set of techniques and original approaches were employed to monitor development of a disease and therapeutic effects of the used compositions.

Results

The YB-1 protein and peptide fragments YB-1$_{1-219}$ and YB-1$_{52-219}$ thereof, but without being limiting, were assessed for effectiveness in preventing clinically important signs of developing AD by combined behavioral, morphological, and biochemical studies.

To estimate the ability of the YB-1 protein and peptide fragments YB-1$_{1-219}$ and YB-1$_{52-219}$ thereof to prevent a neurodegenerative process, the following was performed:

a) mice were trained to develop a navigational reflex of finding the save platform in the Morris water maze, which allowed quantifying the level of spatial memory;

b) immunohistochemical and biochemical analyses (DOT-analysis and ELISA) were used to expose the effect of the above preparations on the level of the key AD marker in order to determine the intensity of the neurodegenerative process in OBX mice;

c) the morpho-functional status of neurons in the cerebral cortex and hippocampus of OBX mice was studied to reveal cell pathologies of pyknosis, cytolysis, and vacuolization type.

Training

The effect of three-weeks-long subchronic intranasal injections of recombinant YB-1 protein and fragments YB-1$_{1-219}$ and YB-1$_{52-129}$ thereof on learning abilities and spatial memory of OBX mice used as a model of sporadic AD was analyzed in detail.

Figure 2:
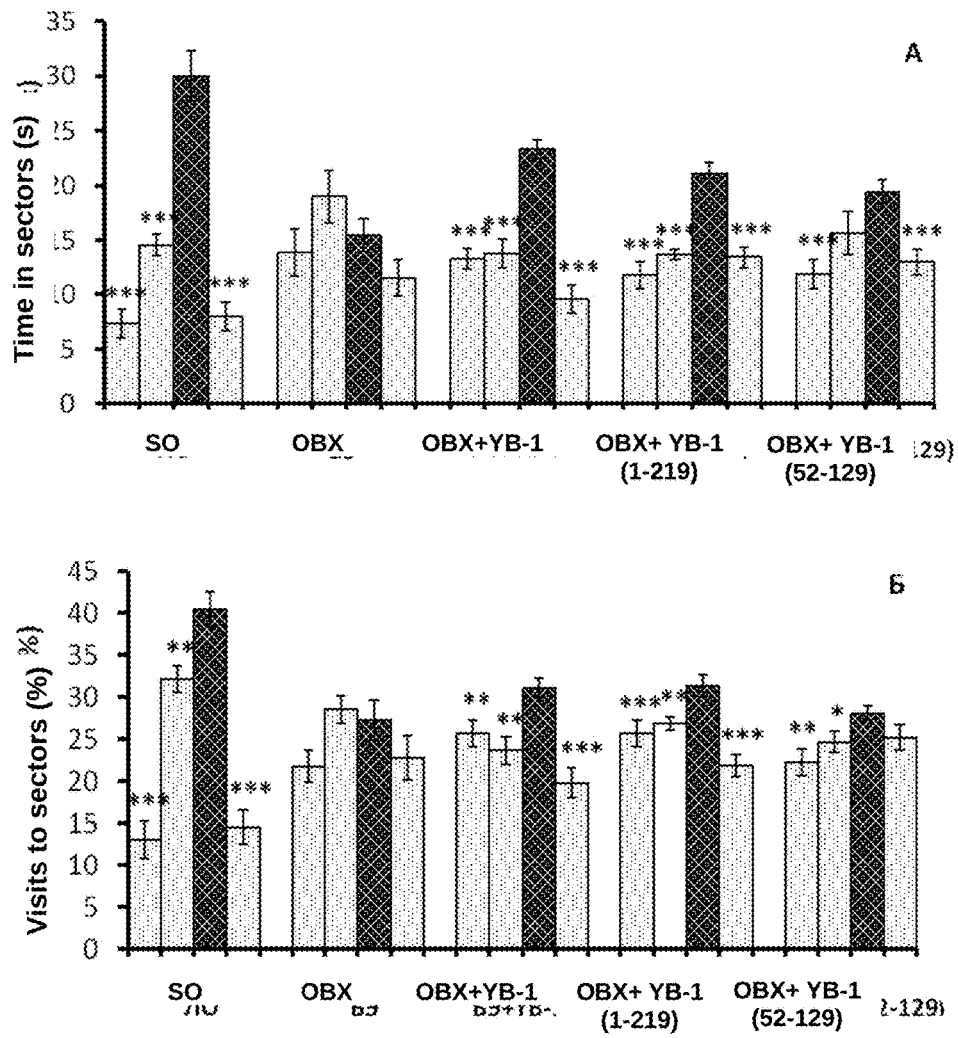
FIG. 2. The effect of intranasally administered YB-1 and fragments $YB-1_{1-219}$ and $YB-1_{52-129}$ thereof on the spatial memory of OBX mice as shown by tests in the water Morris maze. A, Time spent by mice in each maze sector. B, Frequency of visiting each maze sector. Hatched bars represent the target sector. According to the two-way t-test, significant differences are * $p<0.05$;  $p<0.01$; * $p<0.001$.

FIG. 2 presents the effect of intranasally administered YB-1 or fragments YB-1$_{1-219}$ and YB-1$_{52-129}$ thereof on spatial memory of OBX mice as demonstrated by tests in the water Morris maze. A, Time spent by mice in each maze sector. B, Frequency of visiting each maze sector. Hatched bars represent the target sector. According to the two-way t-test, significant differences are * p<0.05;  p<0.01; * p<0.001.

These results show severe memory impairment in OBX mice, except individuals treated with intranasally administered YB-1 or fragment YB-1$_{1-219}$ thereof that retained their memory, as follows from the fact that they could find the target sector of the maze which previously contained the save platform. The positive effect was observed for the both estimation criteria. For SO, OBX, and YB-1- or YB-1$_{1-219}$-treated mice, the time spent in the target sector was 30±2.3>15.4±1.5<23.3±0.9, 21.1±1.0 s, respectively. Percentage of visiting the target sector by the total number of visits to all sectors was for SO, OBX, and YB-1- or YB-1$_{1-219}$-treated mice, 40.4±2.1>27.2±2.4<31.1±1.2, 31.3±1.3, respectively.

Thus, spatial memory tests of OBX mice testify that intranasally administered YB-1 prevents impairment of spatial memory caused by bulbectomy.

Biochemistry

To elucidate the molecular mechanisms of the effect of YB-1 and peptide fragments thereof on the AD-type neurodegeneration, influence of these preparations on the level of [beta]-amyloid in OBX mice was studied.

Figure 3:
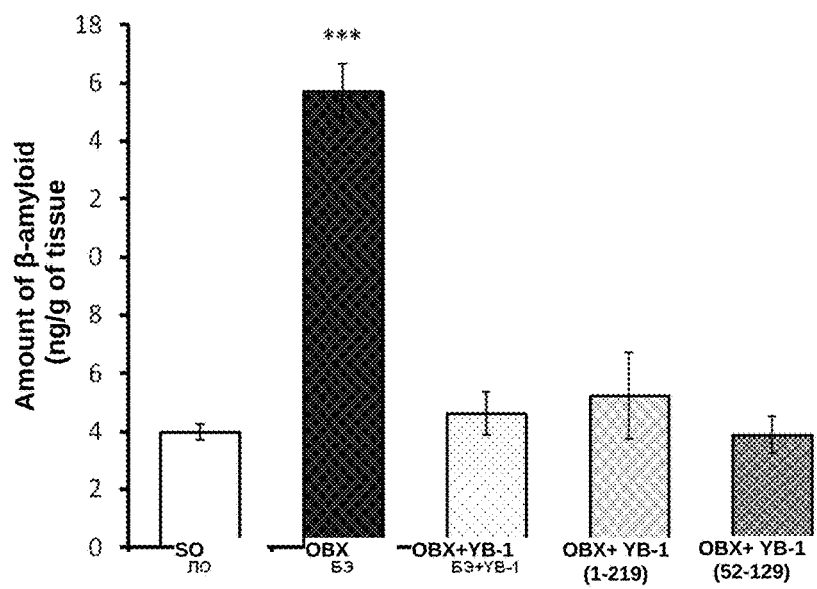
FIG. 3. The effect of intranasally administered YB-1 and fragments $YB-1_{1-219}$ and $YB-1_{52-129}$ thereof on the amount of [beta]-amyloid in the cortex and hippocampus of OBX mice. Ordinate, the amount of [beta]-amyloid protein (ng per g of tissue). According to the two-way t-test, the significant difference is ***$p<0.001$.

FIG. 3 demonstrates the effect of intranasally administered YB-1 and fragments YB-1$_{1-219}$ and YB-1$_{52-129}$ thereof on the amount of [beta]-amyloid in the cortex and hippocampus of OBX mice. Ordinate represents the amount of [beta]-amyloid protein (ng per g tissue). According to the two-way t-test, the significant difference is ***p<0.001.

As found, [beta]-amyloid in extracts from the cortex and hippocampus of OBX mice treated with YB-1 or fragments YB-1$_{1-219}$ and YB-1$_{52-129}$ thereof remained at the level observed for SO mice (4.0±0.3 ng/g) and amounted to 4.6±0.8, 5.2±1.5 И 3.9±0.7 ng/g tissue, respectively. Meanwhile, [beta]-amyloid detected in OBX mice was 15.8±0.9 ng/g tissue (p<0.001). Presumably, prevention of [beta]-amyloid accumulation in the brain of OBX mice is one of the mechanisms that mediate the neuroprotective effect of YB-1 and/or fragments thereof.

Morphology

The severity of cognitive impairment in patients with AD correlates with the gravity of pathological changes, mainly with the level of dead neurons. Therefore, special attention was paid to analysis of the morpho-functional state of neurons in the memory-responsible brain structures, namely, the temporal cortex and hippocampal areas. It should be stressed that these were the most afflicted brain regions of OBX animals. The bulbectomy caused an increased number of pathological cells in all studied brain structures, their average percentage growing from 18% to 45-50%, with a dramatic growth of proportion of pyknomorphic neurons that were no longer living cells but shrunken outer membranes. Also, an increased number of cytolysis-type cells with damaged outer membranes were observed.

The ability of YB-1 and peptide fragments YB-1$_{1-219}$ and YB-1$_{52-219}$ thereof to prevent the neurodegenerative process was assessed by an analysis of the morpho-functional state of neurons in these brain structures of OBX mice that revealed cell pathologies of pyknosis, cytolysis, and vacuolization type.

FIGS. 4-6 demonstrate the effect of intranasally administered YB-1 and fragments YB-1$_{1-219}$ and YB-1$_{52-219}$ thereof on the morpho-functional state of neurons in the temporal cortex (FIGS. 4A-E) and hippocampal areas CA1-CA2 (FIGS. 5A-E) and CA3-CA4 (FIGS. 6A-E) of OBX mice, where A is percentage of morphologically normal cells by the total number of analyzed cells; B, C, D, show percentage of cells with pathologies of pyknosis, cytolysis, and vacuolization type, respectively; E is the neuronal density. According to the two-way t-test, significant differences relative to sham-operated (SO) mice are *—p<0.05; —p<0.01; *—p<0.001, while those relative to OBX mice are +—p<005; ++—p<0.01; +++—p<0.001.

The above results testify that administered YB-1 and fragments YB-1$_{1-219}$ and YB-1$_{52-129}$ thereof had a positive effect on the morpho-functional state of neurons, as was manifested mostly by a decreased number of pykomorphic cells and cytolysis-type cells in all studied brain structures. Accordingly, the number of functional cells in the cortex and hippocampal areas was increased. The strongest positive neuroprotective effect of the YB-1 protein was observed in the temporal cortex where no reliable negative changes as to the neuronal density, the number of healthy neurons, or the number of pykomorphic and cytolysis-type cells were observed versus SO mice.

Figure 7:
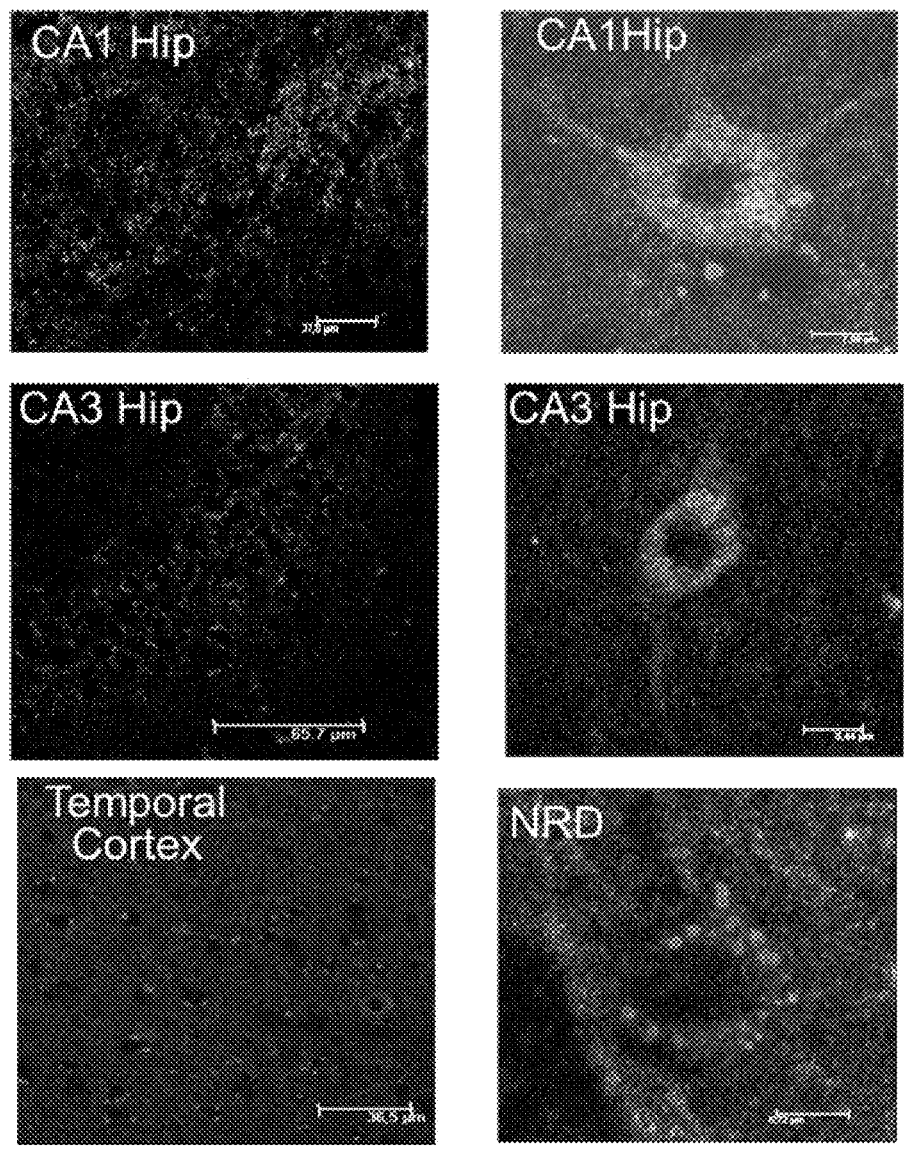
FIG. 7. Penetration of intranasally administered labeled YB-1 into mouse brain regions. CA1 and CA3, hippocampal areas; Temporal cortex; NRD, the serotonin-synthesizing dorsal raphe nucleus of the brainstem. White dots represent labeled YB-1.

Penetration of Labeled YB-1 into Brain Structures and its Localization in Neurons The data on YB-1 ability to overcome the blood-brain barrier in OBX mice are of special interest. YB-1 labeled with fluorescent cyanine dye Cy3 was intranasally administered to mice; 2 h later the mice were decapitated, and brain slices were examined for fluorescence using a confocal microscope. An analysis of the obtained results revealed the largest accumulation of fluorescent granules in such structures as the hippocampus, temporal cortex, serotonin-synthesizing dorsal raphe nucleus of the brainstem, with localization of fluorescent labels in the perinuclear space inside neurons (FIG. 7). In brain slices of control animals treated with the same amount of unlabeled YB-1 no fluorescence was observed.

These results are direct evidence not only for the ability of YB-1 to penetrate into the brain upon its intranasal administration but also for its entering neurons of the AD-afflicted brain regions.

Penetration of Labeled YB-1 into Cultured Eukaryotic Cells.

Figure 8A:
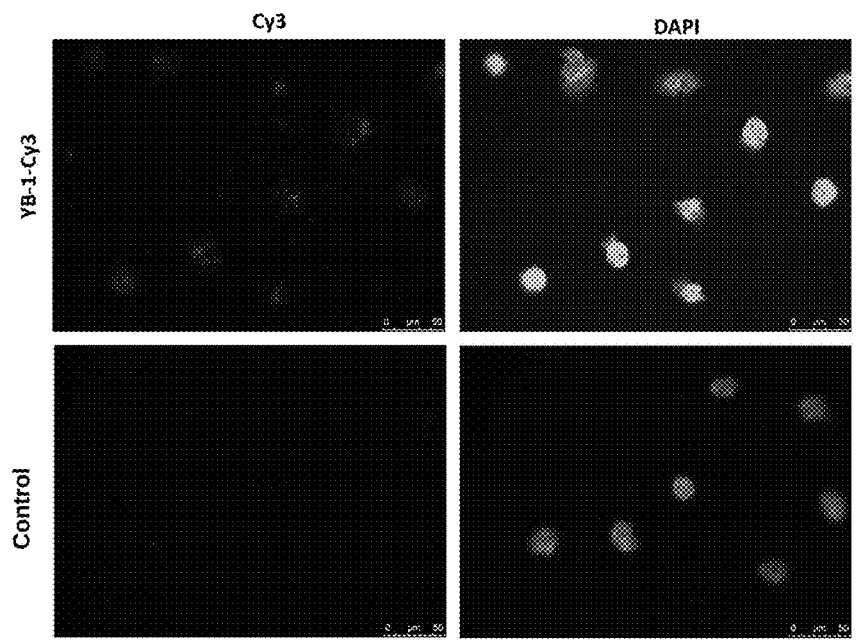
FIG. 8. Penetration of labeled YB-1 into cultured eukaryotic HeLa cells. A, cell smears immediately after incubation with YB-1; B, 4 h after incubation. DAPI, cell nucleus staining dye; non-conjugated dye served as a control.
Figure 8B:
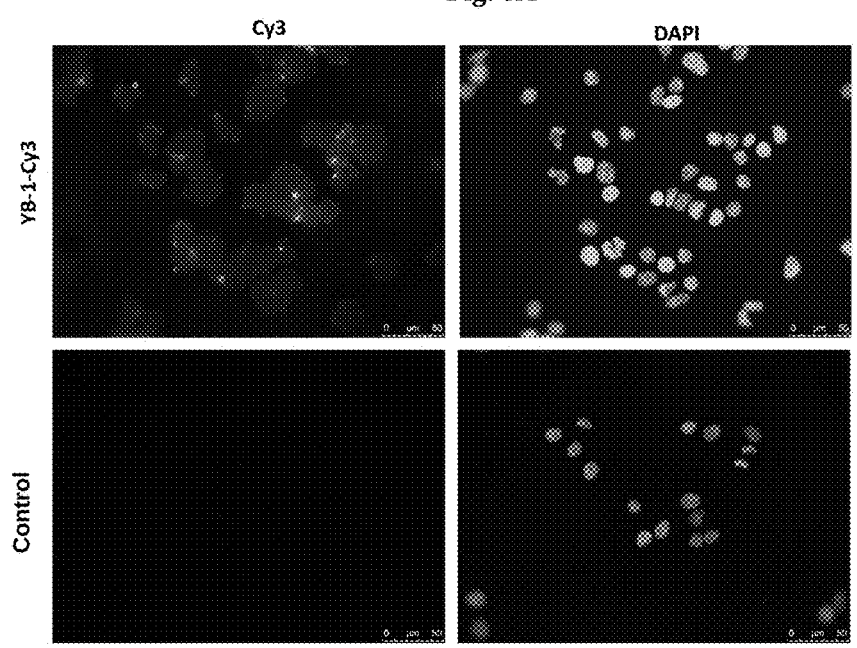

The data on YB-1 capability to penetrate into brain structures are not unambiguously indicative of its ability to permeate through a cell membrane. To address this issue, a model system on the basis of cultured eukaryotic HeLa cells was used. The cells were incubated for 2 h either with fluorescent dye-labeled YB-1 (YB-1-Cy3) or with the dye only that served as a control. After incubation the cells were treated with tripsin, and distribution of fluorescent labels was analyzed either immediately or 4 h after incubation with YB-1. FIG. 8 shows that Cy3 did not penetrate into the HeLa cells. In contrast, Cy3-labeled YB-1 penetrated into the cells and emerged within granular structures in the cytoplasm. It should be noted that 4 h after incubation YB-1-Cy3 was still detected in the cells, which may be indicative of its stability within the cell. The obtained results suggest functional significance of extracellular YB-1 that penetrates into cells.

Thus, the obtained results testify to a neuroprotective effect of the recombinant YB-1 protein and/or fragments thereof manifested as retardation of the AD-type neurodegeneration in OBX mice used as a model of sporadic AD. Besides, they reveal the mechanisms mediating protective functions of the YB-1 protein and/or fragments thereof in neurons of subjects with AD-type neurodegeneration. These mechanisms include a decreased level of cerebral [beta]-amyloid and a potent neuroprotective action that saves a living cell.

The easy method of administration, effectiveness of low dosage that minimizes occurrence of negative side effects, and the possibility of genetic engineering-based production of ample amounts of highly purified YB-1 and/or fragments thereof testify to expediency of development on this basis of a pharmaceutical agent for AD treatment.

INDUSTRIAL APPLICABILITY

The pharmacological composition comprising YB-1 protein or fragment or derivative thereof may be employed in a protective or treatment capacity. Highly efficient compositions based on YB-1 protein or fragment or derivative thereof that further comprise one or more amino acids, deletions, and/or substitutions can provide increased effectiveness and shortened time of the AD treatment.

The pharmacological composition is nontoxic and displays biocompatibility with mammalian organisms, including humans, because its key element is recombinant YB-1 or fragment thereof. Low toxicity of the composition allows increased effectiveness of the treatment due to concurrent combined effects of YB-1 protein or fragments thereof and other drugs and biologically active agents. This is especially important for treatment of related diseases by which the AD treatment is complicated.

The composition has a high solubility and rapidly penetrates into the extracellular space of the organism, which allows treating diseases of the brain. The composition is compatible with any pharmaceutically suitable carriers without reducing the biological activity of the protein YB-1 and/or fragments thereof. The above described results are experimental evidence for effectiveness of the use of YB-2 protein and/or fragments thereof for the treatment of developing AD-type neurodegeneration. The easy method of administration, effectiveness of low dosage, and the possibility of genetic engineering-based production of ample amounts of highly purified YB-1 and/or fragments thereof minimize occurrence of negative side effects.

REFERENCES

1. Bobkova N. V., Nesterova I. V., Nesterov V. I. Status of cholinergic forebrain structures in bulbectomized mice/Bull Exp Biol Med. 2001. V. 131. P. 507-511 [Rus].
2. Bobkova N. V., Nesterova I. V., Medvinskaya N. I., Aleksandrova I. Y., Samokhin A. N., Gershovich Y. G. Post-bulbectomy activation of compensatory mechanisms in the brain/Ross Fiziol Zh Im I M Sechenova. 2004. V. 90. No8. P. 199-200 [Rus].
3. Bobkova N. V., Nesterova I. V., Medvinskaya N. I., Aleksandrova I. Y., Samokhin A. N., Gershovich Y. G., Gershovich P. M., Yashin V. A. Possible role of olfactory system in Alzheimer's disease genesis/In book «Alzheimer's and Parkinson's disease—AD/PD». Edit. L. Hanin, A. Fisher, Monduzzi. Medimond. 2005. P. 91-95.
4. Bobkova N. V. A model of sporadic Alzheimer's disease using bulbectomized animals/In book "Neurodegenerative diseases. Fundamental and applied aspects"/Edit. M. V. Ugryumov. M. Nauka. 2010. P. 341-350 [Rus].
5. Nesterova I. V., Bobkova N. V., Medvinskaya N. I., Samokhin A. N., Alexandrova I. Y. Morphofunctional state of neurons in the temporal cortex and hippocampus in relation to the level of spatial memory in rats after ablation of the olfactory bulbs/Neurosci. Behav. Physiol. 2008. V. 38. No 4. P. 349-353.
6. Gavrilova S. I. Alzheimer's disease: clinics and diagnostics/In book "Neurodegenerative diseases. Fundamental and applied aspects". Edit. M. V. Ugryumov. M. Nauka. 2010. P. 243-251 [Rus].
7. Bachurin S. O., Voronina T. A., Gavrilova S. I., Alesenko A. V., Podolski I. Y., Shevtsova E. F. Modern approaches to treatment of Alzheimer's disease/In book "Neurodegenerative diseases. Fundamental and applied aspects". Edit. M. V. Ugryumov. M. Nauka. 2010. P. 313-340 [Rus].
8. Gavrilova S. I., Kalin Y. B. Social and environmental factors and the mental health of elderly people/Vestn Ross Akad Med Nauk. 2002. V. 9. P. 15-20.
9. Bertoni-Freddari C., Fattoretti P., Casoli T., Caselli U., Meier-Ruge W. Deterioration threshold of synaptic morphology in aging and senile dementia of Alzheimer's type/Anal Quant Cytol Histol. 1996. V. 18. N3. P. 209-13.
10. Su J. H., Anderson A. J., Cummings B. J., Cotman C. W. Immunohistochemical evidence for apoptosis in Alzheimer's disease/Neuroreport. 1994. V. 5. N18. P. 2529-33.
11. Eliseeva I. A., Kim E. R., Guryanov S. G., Ovchinnikov L. P., Lyabin D. N. Y-box binding protein (YB-1) and its functions/Biochemistry (Mosc). 2011. V. 1. P. 65-132 [Rus].
12. Kohno, K., Izumi, H., Uchiumi, T., Ashizuka, M. and Kuwano, M. The pleiotropic functions of the Y-boxbinding protein, YB-1/Bioessays. 2003. V. 25. P. 691-698.
13. Skabkin M. A., Evdokimova V., Thomas A. A. and Ovchinnikov L. P. The major messenger ribonucleoprotein particle protein p50 (YB-1) promotes nucleic acid strand annealing/J. Biol. Chem. 2001. V. 276. P. 44841-44847.
14. Ise, T., Nagatani, G., Imamura, T., Kato, K., Takano, H., Nomoto, M., Izumi, H., Ohmori, H., Okamoto, T., Ohga, T., Uchiumi, T., Kuwano, M. and Kohno, K. Transcription factor Y-box binding protein 1 binds preferentially to cisplatin-modified DNA and interacts with proliferating cell nuclear antigen/Cancer Res. 1999. V. 59. P. 342-346.

15. Chansky, H. A., Hu, M., Hickstein, D. D. and Yang, L. Oncogenic TLS/ERG and EWS/Fli-1 fusion proteins inhibit RNA splicing mediated by YB-1 protein/Cancer Res. 2001.V. 61. P. 3586-3590.
16. Skabkin M. A., Kiselyova O. I., Chernov K. G., Sorokin A. V., Dubrovin E. V., Yaminsky I. V., Vasiliev V. D. and Ovchinnikov L. P. Structural organization of mRNA complexes with major core mRNP protein YB-1/Nucleic Acids Res. 2004. V. 32. P. 5621-5635.
17. Davydova, E. K., Evdokimova, V. M., Ovchinnikov, L. P. and Hershey, J. W. Overexpression in COS cells of p50, the major core protein associated with mRNA, results in translation inhibition/Nucleic Acids Res. 1997. V. 25. P. 2911-2916.
18. Evdokimova, V., Ruzanov, P., Imataka, H., Raught, B., Svitkin, Y., Ovchinnikov, L. P. and Sonenberg, N. The major mRNA-associated protein YB-1 is a potent 5' cap-dependent mRNA stabilizer/EMBO J. 2001. V. 20. P. 5491-5502.
19. Evdokimova, V., Ruzanov, P., Anglesio, M. S., Sorokin, A. V., Ovchinnikov, L. P., Buckley, J., Triche, T. J., Sonenberg, N., Sorensen, P. H. Akt-Mediated YB-1 Phosphorylation Activates Translation of Silent mRNA Species/Mol. Cell. Biol. 2006. V. 26. N1. P. 277-292.
20. Ruzanov P. V., Evdokimova V. M., Korneeva N. L., Hershey J. W. and Ovchinnikov L. P. Interaction of the universal mRNA-binding protein, p50, with actin: a possible link between mRNA and microfilaments/J. Cell Sci. 1999. V. 112. Pt. 20. P. 3487-3496.
21. Fotovati A., Abu-Ali S., Wang P. S., Deleyrolle L. P., Lee C., Triscott J., Chen J. Y., Franciosi S., Nakamura Y., Sugita Y., Uchiumi T., Kuwano M., Leavitt B. R., Singh S. K., Jury A., Jones C., Wakimoto H., Reynolds B. A., Pallen C. J., Dunn S. E. YB-1 Bridges Neural Stem Cells and Brain Tumor-Initiating Cells via Its Roles in Differentiation and Cell Growth/Cancer Res. 2011. V. 71. No16. P. 5569-78.
22. Stone J. G., Casadesus G., Gustaw-Rothenberg K., Siedlak S. L., Wang X., Zhu X., Perry G., Castellani R. J., Smith M. A. Frontiers in Alzheimer's Disease Therapeutics/Ther Adv Chronic Dis. 2011. V. 2. Nol. P. 9-23.
23. Hanssen L., Frye B. C., Ostendorf T., Alidousty C., Djudjaj S., Boor P., Rauen T., Floege J., Mertens P. R., Raffetseder U. Y-box binding protein-1 mediates profibrotic effects of calcineurin inhibitors in the kidney/J Immunol. 2011. V. 187. N1. 298-308.
24. Lu, Z. H., Books, J. T. and Ley, T. J. YB-1 is important for late-stage embryonic development, optimal cellular stress responses, and the prevention of premature senescence/Mol Cell Biol. 2005. V. 25. P. 4625-4637.
25. Frye B. C., Halfter S., Djudjaj S., Muehlenberg P., Weber S., Raffetseder U., En-Nia A., Knott H., Baron J. M., Dooley S., Bernhagen J., Mertens P. R. Y-box protein-1 is actively secreted through a non-classical pathway and acts as an extracellular mitogen/EMBO Rep. 2009. V. 10. N7. P. 783-9.
26. Rauen T., Raffetseder U., Frye B. C., Djudjaj S., Mbhlenberg P. J., Eitner F., Lendahl U., Bernhagen J., Dooley S., Mertens P. R. YB-1 acts as a ligand for Notch-3 receptors and modulates receptor activation/J Biol Chem. 2009. V. 284. N39. P. 26928-40.
27. Ables J. L., Breunig J. J., Eisch A. J., Rakic P. Not(ch) just development: Notch signalling in the adult brain/Nat Rev Neurosci. 2011. V. 12. N5. P. 269-83.
28. Morris R. G., Anderson E., Lynch G. S., Baudry M. Selection impairment of learning and blockade of long-term potentiation by an N-methyl-D-asportate receptor antagonist, AP5/Nature, 1986, v. 319, p. 774-776.
29. Nudler E., Evgeniev M., Bobkova N. THE USE OF INTRANASALLY ADMINISTERED HSP70 PROTEIN TO TREAT NEURODEGENERATIVE DISEASES/PCT appl. WO2013006076 (2013-01-10)
30. Guryanov S. G., Selivanova O. M., Nikulin A. D., Enin G. A., Melnik B. S., Kretov D. A., Serdyuk I. N., Ovchinnikov L. P. Formation of amyloid-like fibrils by Y-box binding protein 1 (YB-1) is mediated by its cold shock domain and modulated by disordered terminal domains/PLoS One. 2012; 7(5):e36969. Epub 2012 May 8.
31. Studier F. W. Protein production by auto-induction in high-density shaking cultures/Prot. Exp. Pur. (2005) 41, 207-234

---

The invention claimed is:

1. A method of treating a subject having Alzheimer's disease (AD), comprising intranasally administering to the subject a therapeutically effective amount of YB-1 protein or an active fragment thereof, selected from YB-1$_{1-219}$ and YB-1$_{52-129}$.

2. The method of claim 1, wherein a therapeutically effective amount of active fragments of the protein YB-1 are administered to the subject.

3. The method of claim 1, wherein the YB-1 protein comprises a full-length YB-1$_{1-324}$ protein.

4. The method of claim 3, wherein the YB-1$_{1-324}$ protein has the amino acid sequence represented by SEQ ID NO: 1 or SEQ ID NO: 7.

5. The method of claim 1, wherein the YB-1 protein or an active fragment thereof is formulated either individually or in a therapeutically effective composition further comprising one or more agents facilitating brain delivery of this intranasally administered composition.

6. The method of claim 1, wherein the subject is human.

7. The method of claim 1, wherein the therapeutically effective amount of YB-1 protein or an active fragment thereof administered is within the range from 0.2 mcg to 1 mg per kg body weight per day.

8. The method of claim 1, wherein the YB-1$_{1-324}$ protein is a) polypeptide having the amino acid sequence SEQ ID NO: 1 or b) polypeptide having the amino acid sequence which has 98% identity to amino acid sequence of SEQ ID NO: 1.

9. The method of claim 1, wherein the active protein fragment YB-1$_{1-219}$ has the amino acid sequence represented by SEQ ID NO: 3 or SEQ ID NO: 9.

10. The method of claim 1, wherein the active protein fragment YB-1$_{52-129}$ has the amino acid sequence represented by SEQ ID NO: 5 or SEQ ID NO: 11.

* * * * *